United States Patent
Zhai et al.

(10) Patent No.: US 11,850,239 B2
(45) Date of Patent: Dec. 26, 2023

(54) MDM2 INHIBITOR AND A PLATINUM COMPOUND FOR CANCER TREATMENT

(71) Applicants: Ascentage Pharma (Suzhou) Co., Ltd., Suzhou (CN); Ascentage Pharma Group Corp Limited, Hong Kong (CN)

(72) Inventors: Yifan Zhai, Suzhou (CN); Dajun Yang, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 253 days.

(21) Appl. No.: 17/127,131

(22) Filed: Dec. 18, 2020

(65) Prior Publication Data

US 2021/0186939 A1    Jun. 24, 2021

Related U.S. Application Data

(60) Provisional application No. 62/950,743, filed on Dec. 19, 2019.

(51) Int. Cl.
| | |
|---|---|
| *A61K 31/437* | (2006.01) |
| *A61K 31/282* | (2006.01) |
| *A61P 35/00* | (2006.01) |
| *A61K 33/243* | (2019.01) |
| *A61K 31/407* | (2006.01) |
| *A61K 31/555* | (2006.01) |

(52) U.S. Cl.
CPC .......... *A61K 31/437* (2013.01); *A61K 31/282* (2013.01); *A61K 31/407* (2013.01); *A61K 31/555* (2013.01); *A61K 33/243* (2019.01); *A61P 35/00* (2018.01)

(58) Field of Classification Search
None
See application file for complete search history.

(56) References Cited

FOREIGN PATENT DOCUMENTS

| WO | WO 2015/161032 A1 | 10/2015 |
|---|---|---|
| WO | WO 2017/176957 A1 | 10/2017 |
| WO | WO 2017/176958 A1 | 10/2017 |
| WO | WO 2018/220126 A1 | 12/2018 |
| WO | WO 2019/165189 A1 | 8/2019 |
| WO | WO 2019/173516 A1 | 9/2019 |
| WO | WO 2019/246570 A1 | 12/2019 |

OTHER PUBLICATIONS

Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," *J. Med. Chem.*, 60(7): 2819-2839 (2017).

Yi et al., "A novel small molecule inhibitor of MDM2-p53 (APG-115) enhances radiosensitivity of gastric adenocarcinoma," *Journal of Experimental & Clinical Cancer Research*, 37: 97, 10 pages (2018).

Khoury et al., "P53 Mdm2 Inhibitors," *Curr. Pharm. Des.* 18(30): 4668-4678 (2012).

NCT03781986: A Study of APG-115 in Patients With Salivary Gland Carcinoma, First Posted Dec. 20, 2018 (Submitted Date Dec. 18, 2018), Last Update Posted Feb. 15, 2021, downloaded May 3, 2021 from internet: https://clinicaltrials.gov/ct2/show/NCT03781986?term=NCT03781986&draw=2&rank=1.

*Primary Examiner* — Brian J Davis
(74) *Attorney, Agent, or Firm* — Jones Day

(57) ABSTRACT

Provided herein is a method of treating, preventing, or alleviating one or more symptoms of a disorder, disease, or condition mediated by an MDM2 with an MDM2 inhibitor, e.g., a compound of Formula (I), and a platinum compound. Also provided herein is a method of inhibiting the growth of a cell with an MDM2 inhibitor and a platinum compound.

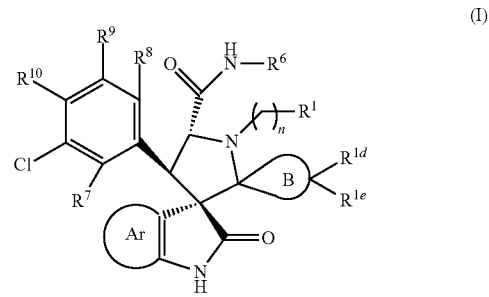

(I)

20 Claims, No Drawings

MDM2 INHIBITOR AND A PLATINUM COMPOUND FOR CANCER TREATMENT

CROSS-REFERENCE TO RELATED APPLICATIONS

This application claims the benefit of U.S. Provisional Application No. 62/950,743, filed Dec. 19, 2019, the entirety of which is incorporated herein by reference.

FIELD

Provided herein is a method of treating, preventing, or alleviating one or more symptoms of a disorder, disease, or condition mediated by an MDM2 with an MDM2 inhibitor and a platinum compound. Also provided herein is a method of inhibiting the growth of a cell with an MDM2 inhibitor and a platinum compound.

BACKGROUND

The p53 tumor suppressor is a key transcription factor that controls the life and death of a cell. Vousden & Lu, *Nat. Rev Cancer* 2002, 2, 594-604. It acts as an important defense mechanism against cancer onset and progression. Nag et al., *J. Biomed. Res.* 2013, 27, 254-271. As the cellular gatekeeper, p53 is activated in response to oncogenic stress stimuli, resulting in the inhibition of tumor-cell growth. Balint & Vousden, *Br. J. Cancer* 2001, 85, 1813-1823. However, the tumor-suppression function of p53 is compromised in almost all human cancer. Issaeva, *Cancers (Basel)* 2019, 11, E332; Kocik et al., *Cancers (Basel)* 2019, 11, E1014. In about half of all human cancer, the p53 is inactivated by loss-of-function mutations/deletions in the TP53 gene encoding p53. Kocik et al., *Cancers (Basel)* 2019, 11, E1014. In the remaining cancer, p53 function is inhibited primarily by the murine double minute 2 (MDM2) protein via a direct protein-protein interaction. Shangary et al., *Clin. Cancer Res.* 2008, 14, 5318-4324.

MDM2 is a primary negative regulator of p53. Kubbutat et al., *Nature* 1997, 387, 299-303; Shi and Gu, *Genes Cancer* 2012, 3, 240-248. In the absence of stress, MDM2 binds to the transactivation domain of p53, preventing it from binding to DNA and marking it for proteasomal degradation. Id. In this way, MDM2-p53 interaction limits p53 abundance and p53-mediated tumor-suppressor functions. Id. Aberrant MDM2 expression restricts p53 and its tumor-suppressor functions, leaving cells more susceptible to oncogenic mutations, transformation, and subsequent tumor growth. Oliner et al., *Nature* 1993, 362, 857-860; Kussie et al., *Science* 1996, 274, 948-953; Bond et al., *Cell* 2004, 119, 591-602; Oliner et al., *Cold Spring Harb. Perspect. Med.* 2016, 6, a026336. Preclinical data have shown that blocking MDM2-p53 interactions by a small molecule MDM2 inhibitor induce apoptosis in both MDM2-overexpressing and wild-type tumor cell lines, thus demonstrating that small molecule inhibitors designed to block the MDM2-p53 interaction can liberate the tumor suppressor function of wild-type p53. Vassilev, *Trends Mol. Med.* 2007, 13, 23-31; Vu & Vassilev, *Curr. Top. Microbiol. Immunol.* 2011, 348, 151-172; Chen et al., *Oncotarget* 2017, 8, 43008-43022; Aguilar et al., *J. Med. Chem.* 2017, 60, 2819-2839.

Despite the advances in cancer treatment, cancer remains a major worldwide public health problem. It was estimated that there will be 1,762,450 new cancer cases diagnosed and 606,880 cancer deaths in the US alone in 2019. *Cancer Facts & Figures* 2019. Therefore, there is still a need for an effective therapy for cancer.

SUMMARY OF THE DISCLOSURE

Provided herein is a method of treating, preventing, or alleviating one or more symptoms of a disorder, disease, or condition mediated by an MDM2 in a subject, comprising administering to the subject a therapeutically effective amount of an MDM2 inhibitor and a therapeutically effective amount of a platinum compound; wherein the MDM2 inhibitor is a compound of Formula (I):

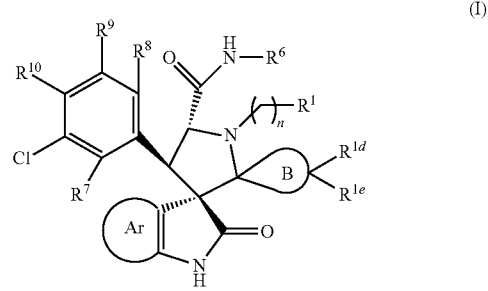

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

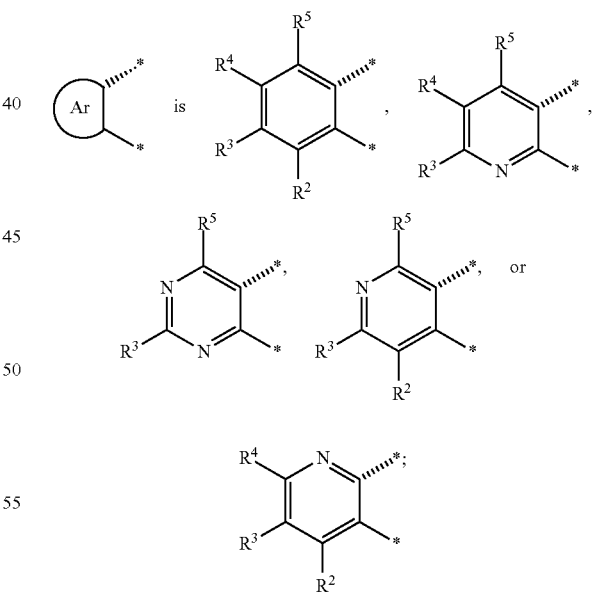

ring B is $C_{3-10}$ cycloalkyl or heterocyclyl;

$R^1$ is hydrogen, $C_{1-6}$ alkyl, $C_{3-10}$ cycloalkyl, heterocyclyl, $-NR^{1b}R^{1c}$, or $-OR^{1a}$;

n is an integer of 0, 1, or 2;

$R^2$, $R^3$, $R^4$, $R^5$, $R^7$, $R^8$, $R^9$, and $R^{10}$ are each independently hydrogen, fluoro, chloro, methyl, or trifluoromethyl;

$R^6$ is

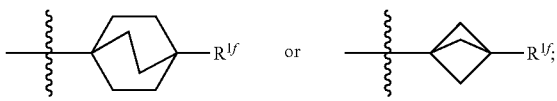

wherein each $R^{1f}$ is independently —C(=O)OR$^{1a}$, —C(=O)NR$^{1b}$R$^{1c}$, or —C(=O)NHSO$_2$CH$_3$;

$R^{1d}$ and $R^{1e}$ are each independently hydrogen, halo, $C_{1-6}$ alkyl, or —OR$^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Also provided herein is a method of treating, preventing, or alleviating one or more symptoms of a disorder, disease, or condition mediated by an MDM2/p53 interaction in a subject, comprising administering to the subject (i) a therapeutically effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) a therapeutically effective amount of a platinum compound.

Furthermore provided herein is a method of treating, preventing, or alleviating one or more symptoms of cancer in a subject, comprising administering to the subject (i) a therapeutically effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) a therapeutically effective amount of a platinum compound. In one embodiment, the cancer has a functional p53. In another embodiment, the cancer has a wild-type p53.

Additionally, provided herein is a method of inhibiting the growth of a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound. In one embodiment, the cell has a functional p53. In another embodiment, the cell has a wild-type p53.

Provided herein is a method of modulating the activity of MDM2 in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound. In one embodiment, the cell has a functional p53. In another embodiment, the cell has a wild-type p53.

Provided herein is a method of modulating an MDM2/p53 interaction in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound. In one embodiment, the cell has a functional p53. In another embodiment, the cell has a wild-type p53.

Provided herein is a method of inducing apoptosis in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound. In one embodiment, the cell has a functional p53. In another embodiment, the cell has a wild-type p53.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., *Remington: The Science and Practice of Pharmacy,* 22nd ed.; Allen Ed.: Philadelphia, PA, 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$)

carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1]pentyl, bicyclo[2.1.1]hexyl, bicyclo[2.2.1]heptyl, bicyclo[2.2.2]octyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, 3-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(O)S$R^a$, —C(N$R^a$)N$R^b R^c$, —C(S)$R^a$, —C(S)O$R^a$, —C(S)N$R^b R^c$, —O$R^a$, —OC(O)$R^a$, —OC(O)O$R^a$, —OC(O)N$R^b R^c$, —OC(O)S$R^a$, —OC(=N$R^a$)N$R^b R^c$, —OC(S)$R^a$, —OC(S)O$R^a$, —OC(S)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(O)S$R^d$, —N$R^a$C(=N$R^d$)N$R^b R^c$, —N$R^a$C(S)$R^d$, —N$R^a$C(S)O$R^d$, —N$R^a$C(S)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$)N$R^f R^g$, —C(S)$R^e$, —C(S)O$R^e$, —C(S)N$R^f R^g$, —OC(O)$R^e$, —OC(O)O$R^e$, —OC(O)N$R^f R^g$, —OC(O)S$R^e$, —OC(=N$R^e$)N$R^f R^g$, —OC(S)$R^e$, —OC(S)O$R^e$, —OC(S)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(=N$R^h$)N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{125}$I) iodine-127 ($^{127}$I) iodine-129 ($^{129}$I) and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 IN) nitrogen-15 ($^{15}$N), oxygen-16 ($^{16}$O), oxygen-17 ($^{17}$O), oxygen-18 ($^{18}$O) fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I) iodine-125 ($^{125}$I) iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1H$), deuterium ($^2H$ or D), and tritium ($^3H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a diastereomer, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) a diastereomer, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of a diastereomer, a mixture of two or more diastereomers, a tautomer, a mixture of two or more tautomers, or an isotopic variant of the compound referenced therein."

MDM2 Inhibitors

In one embodiment, the MDM2 inhibitor provided herein is a compound of Formula (I):

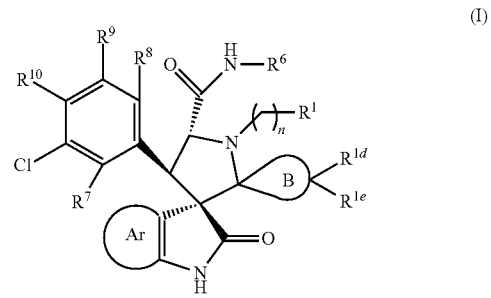

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

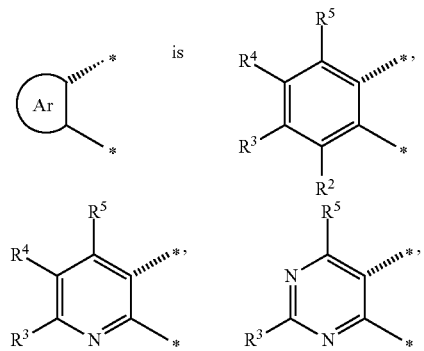

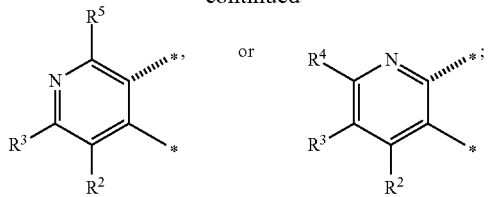

ring B is $C_{3-10}$ cycloalkyl or heterocyclyl;

$R^1$ is hydrogen, $C_{1-6}$ alkyl, $C_{3-10}$ cycloalkyl, heterocyclyl, $-NR^{1b}R^{1c}$, or $-OR^{1a}$; and n is an integer of 0, 1, or 2;

$R^2$, $R^3$, $R^4$, $R^5$, $R^7$, $R^8$, $R^9$, and $R^{10}$ are each independently hydrogen, fluoro, chloro, methyl, or trifluoromethyl;

$R^6$ is

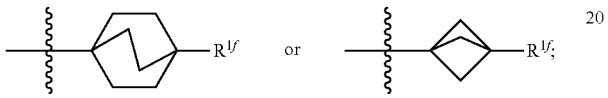

wherein each $R^{1f}$ is independently $-C(=O)OR^{1a}$, $-C(=O)NR^{1b}R^{1c}$, or $-C(=O)NHSO_2CH_3$;

$R^{1d}$ and $R^{1e}$ are each independently hydrogen, halo, $C_{1-6}$ alkyl, or $-OR^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) $-C(O)R^a$, $-C(O)OR^a$, $-C(O)NR^bR^c$, $-C(O)SR^a$, $-C(NR^a)NR^bR^c$, $-C(S)R^a$, $-C(S)OR^a$, $-C(S)NR^b$ $R^c$, $-OR^a$, $-OC(O)R^a$, $-OC(O)OR^a$, $-OC(O)NR^b$ $R^c$, $-OC(O)SR^a$, $-OC(=NR^a)NR^bR^c$, $-OC(S)R^a$, $-OC(S)OR^a$, $-OC(S)NR^bR^c$, $-OS(O)R^a$, $-OS(O)_2$ $R^a$, $-OS(O)NR^bR^c$, $-OS(O)_2NR^bR^c$, $-NR^bR^c$, $-NR^aC(O)R^d$, $-NR^aC(O)OR^d$, $-NR^aC(O)NR^bR^c$, $-XNR^aC(O)SR^d$, $-NR^aC(=NR^a)NR^bR^c$, $-NR^aC(S)R^d$, $-NR^aC(S)OR^d$, $-NR^aC(S)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(O)$ $SR^e$, $-C(NR^e)NR^fR^g$, $-C(S)R^e$, $-C(S)OR^e$, $-C(S)$ $NR^fR^g$, $-OR^e$, $-OC(O)R^e$, $-OC(O)OR^e$, $-OC(O)$ $NR^fR^g$, $-OC(O)SR^e$, $-OC(=NR^e)NR^fR^g$, $-OC(S)$ $R^e$, $-OC(S)OR^e$, $-OC(S)NR^fR^g$, $-OS(O)R^e$, $-OS$ $(O)_2R^e$, $-OS(O)NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(O)SR^f$, $-NR^eC(=NR^h)NR^fR^g$, $-NR^eC(S)$ $R^h$, $-NR^eC(S)OR^f$, $-NR^eC(S)NR^fR^g$, $-NR^eS(O)R^h$, $-NR^eS(O)_2R^h$, $-NR^eS(O)NR^fR^g$, $-NR^eS(O)_2NR^f$ $R^g$, $-S(O)R^e$, $-S(O)_2R^e$, $-S(O)NR^fR^g$, and $-S(O)_2$ $NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, in Formula (I),

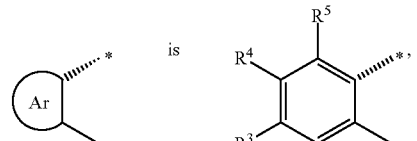

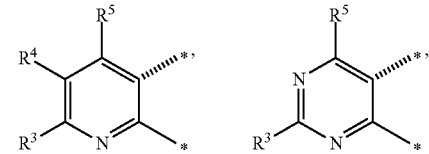

ring B is $C_{3-10}$ cycloalkyl or heterocyclyl;

$R^1$ is hydrogen, $C_{1-6}$ alkyl, $C_{3-10}$ cycloalkyl, heterocyclyl, $-NR^{1b}R^{1c}$, or $-OR^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

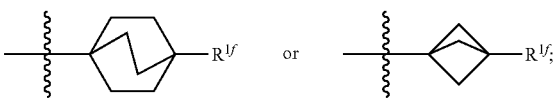

wherein each $R^{1f}$ is independently $-C(=O)OR^{1a}$, $-C(=O)NR^{1b}R^{1c}$, or $-C(=O)NHSO_2CH_3$;

$R^7$ is fluoro;

$R^{1d}$ and $R^{1e}$ are each independently hydrogen, halo, $C_{1-6}$ alkyl, or $-OR^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (I),

Ar is

[structure: phenyl with R⁵, R⁴, R³, R² substituents] or [structure: pyridyl with R⁵, R³, R² substituents];

ring B is $C_{3-10}$ cycloalkyl;
$R^1$ is hydrogen or $C_{1-6}$ alkyl; and n is an integer of 0, 1, or 2;
$R^2$, $R^4$, $R^5$, $R^8$, $R^9$, and $R^{10}$ are each independently hydrogen, fluoro, chloro, methyl, or trifluoromethyl;
$R^3$ is chloro;
$R^6$ is

[structure: bicyclo substituent–$R^{1f}$] or [structure: bicyclobutyl–$R^{1f}$];

wherein each $R^{1f}$ is independently —C(=O)O$R^{1a}$, —C(=O)N$R^{1b}R^{1c}$, —C(=O)NHSO$_2$CH$_3$;
$R^7$ is fluoro;
$R^{1d}$ and $R^{1e}$ are each independently hydrogen, halo, $C_{1-6}$ alkyl, or —O$R^{1a}$; and
each $R^{1a}$, $R^{1b}$, and $R^{1c}$ is independently hydrogen or $C_{1-6}$ alkyl;
wherein each alkyl is independently substituted with one or more, in one embodiment, one, two, three, or four, substituents Q.

In yet another embodiment, in Formula (I),

Ar is [structure: phenyl] or [structure: pyridyl];

ring B is cyclohexyl or cyclobutyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;
$R^6$ is

[structure: bicyclo–$R^{1f}$] or [structure: bicyclobutyl–$R^{1f}$];

wherein each $R^{1f}$ is independently —C(=O)OH, —C(=O)NH$_2$, or —C(=O)NHSO$_2$CH$_3$;
$R^7$ is fluoro; and
$R^{1d}$ and $R^{1e}$ are each independently hydrogen, fluoro, methyl, or hydroxy.

In still another embodiment, in Formula (I),

Ar is [structure: phenyl] or [structure: pyridyl];

ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;
$R^6$ is

[structure: bicyclo–$R^{1f}$] or [structure: bicyclobutyl–$R^{1f}$];

wherein each $R^{1f}$ is independently —C(=O)OH, —C(=O)NH$_2$, or —C(=O)NHSO$_2$CH$_3$; and
$R^7$ is fluoro.

In another embodiment, the MDM2 inhibitor provided herein is a compound of Formula (II):

(II)

[chemical structure of Formula (II)]

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^7$, $R^8$, $R^9$, $R^{10}$, $R^{1d}$, $R^{1e}$, $R^{1f}$, ring Ar, ring B, and n are each as defined herein.

In yet another embodiment, the MDM2 inhibitor provided herein is a compound of Formula (III):

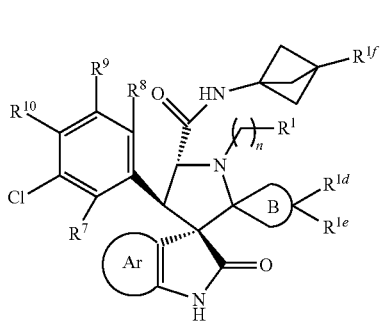

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^7$, $R^8$, $R^9$, $R^{10}$, $R^{1d}R^{1e}$, $R^{1f}$, ring Ar, ring B, and n are each as defined herein.

In one embodiment, in Formula (II) or (III),

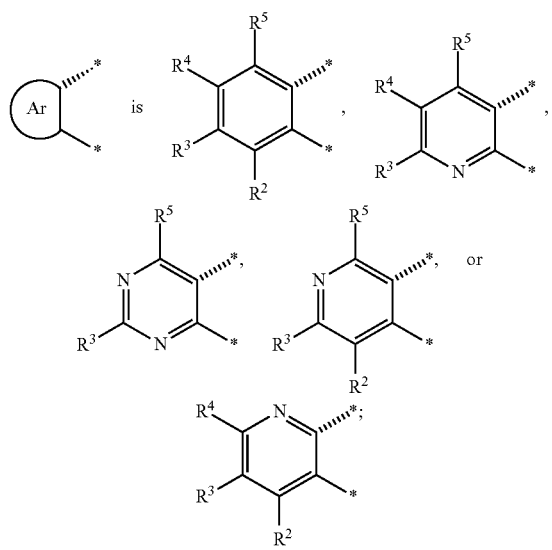

ring B is $C_{3-10}$ cycloalkyl or heterocyclyl;
$R^1$ is hydrogen, $C_{1-6}$ alkyl, $C_{3-10}$ cycloalkyl, heterocyclyl, —$NR^{1b}$ or —$OR^{1a}$; and n is an integer of 0, 1, or 2;
$R^2$, $R^4$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or —$OR^{1a}$; or $R^{1d}$ and $R^{1e}$ together with the carbon to which they are attached form $C_{3-10}$ cycloalkyl or heterocyclyl; and
$R^{1f}$ is $C(=O)OR^{1a}$, —$C(=O)NR^{1b}R^{1c}$, or —$C(=O)NHSO_2CH_3$; and
each $R^{1a}$, $R^{1b}$, and $R^{1c}$ is independently hydrogen or $C_{1-6}$ alkyl;
wherein each alkyl, cycloalkyl, and heterocyclyl is optionally substituted with one or more, in one embodiment, one, two, three, or four, substituents Q.

In another embodiment, in Formula (II) or (III),

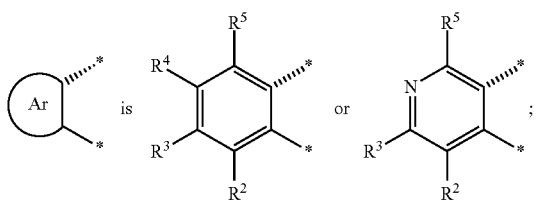

ring B is $C_{3-10}$ cycloalkyl;
$R^1$ is hydrogen or $C_{1-6}$ alkyl; and n is an integer of 0, 1, or 2;
$R^2$, $R^4$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or —$OR^{1a}$;
$R^{1f}$ is —$C(=O)OR^{1a}$, —$C(=O)NR^{1b}R^{1c}$, or —$C(=O)NHSO_2CH_3$; and
each $R^{1a}$, $R^{1b}$, and $R^{1c}$ is independently hydrogen or $C_{1-6}$ alkyl;
wherein each alkyl is independently substituted with one or more, in one embodiment, one, two, three, or four, substituents Q.

In yet another embodiment, in Formula (II) or (III),

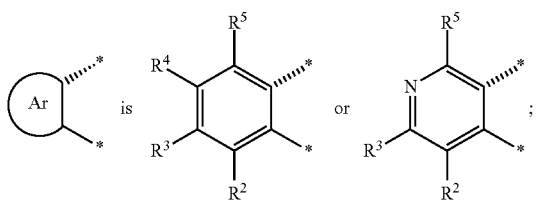

ring B is cyclohexyl or cyclobutyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;
$R^7$ is fluoro;
$R^{1d}$ and $R^{1e}$ are each independently hydrogen, fluoro, methyl, or hydroxy; and
$R^{1f}$ is —$C(=O)OH$, —$C(=O)NH_2$, or —$C(=O)NHSO_2CH_3$.

In still another embodiment, in Formula (II) or (III),

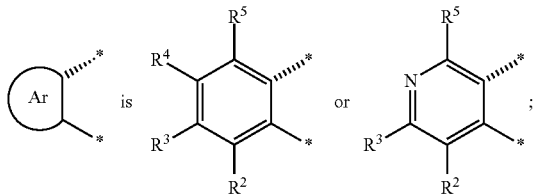

ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;

$R^7$ is fluoro; and $R^{1f}$ is —C(=O)OH, —C(=O)NH$_2$, or —C(=O)NHSO$_2$CH$_3$.

In yet another embodiment, the MDM2 inhibitor provided herein is a compound of Formula (IV):

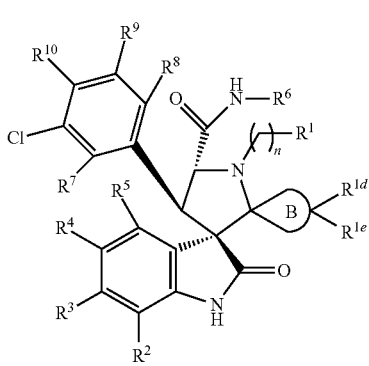

(IV)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^8$, $R^9$, $R^{10}$, $R^{1d}$, $R^{1e}$, ring B, and n are each as defined herein.

In one embodiment, in Formula (IV), ring B is C$_{3-10}$ cycloalkyl or heterocyclyl;

$R^1$ is hydrogen, C$_{1-6}$ alkyl, C$_{3-10}$ cycloalkyl, heterocyclyl, or —OR$^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

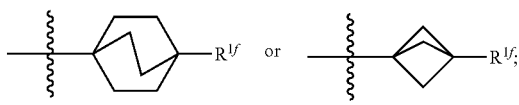

wherein each $R^{1f}$ is independently —C(=O)OR$^{1a}$, —C(=O)NR$^{1b}$R$^{1c}$, or —C(=O)NHSO$_2$CH$_3$;

$R^7$ is fluoro;

$R^{1d}$ and $R^{1e}$ are each independently hydrogen, halo, C$_{1-6}$ alkyl, or —OR$^{1a}$; or $R^{1d}$ and $R^{1e}$ together with the carbon to which they are attached form C$_{3-10}$ cycloalkyl or heterocyclyl; and each $R^{1a}$, $R^{1b}$, and $R^{1c}$ is independently hydrogen or C$_{1-6}$ alkyl;

wherein each alkyl, cycloalkyl, and heterocyclyl is optionally substituted with one or more, in one embodiment, one, two, three, or four, substituents Q.

In another embodiment, in Formula (IV), ring B is C$_{3-10}$ cycloalkyl;

$R^1$ is hydrogen or C$_{1-6}$ alkyl; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

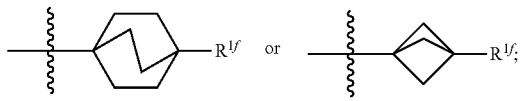

wherein each $R^{1f}$ is independently —C(=O)OR$^{1a}$, —C(=O)NR$^{1b}$R$^{1c}$, or —C(=O)NHSO$_2$CH$_3$;

$R^7$ is fluoro;

$R^{1d}$ and $R^{1c}$ are each independently hydrogen, halo, C$_{1-6}$ alkyl, or OR$^{1a}$; and each $R^{1a}$, $R^{1b}$, and $R^{1c}$ is independently hydrogen or C$_{1-6}$ alkyl;

wherein each alkyl is independently substituted with one or more, in one embodiment, one, two, three, or four, substituents Q.

In yet another embodiment, in Formula (IV), ring B is cyclohexyl or cyclobutyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

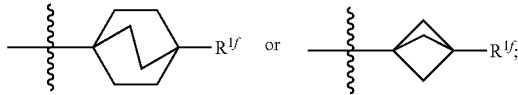

wherein each $R^{1f}$ is independently —C(=O)OH, —C(=O)NH$_2$, or —C(=O)NHSO$_2$CH$_3$;

$R^7$ is fluoro; and $R^{1d}$ and $R^{1e}$ are each independently hydrogen, fluoro, methyl, or hydroxy.

In still another embodiment, in Formula (IV), ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

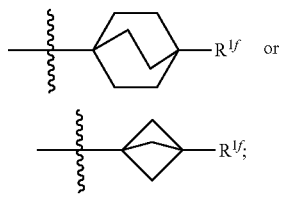

wherein each $R^{1f}$ is independently —C(=O)OH, —C(=O)NH$_2$, or —C(=O)NHSO$_2$CH$_3$; and $R^7$ is fluoro.

In yet another embodiment, the MDM2 inhibitor provided herein is a compound of Formula (V):

(V)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^7$, $R^8$, $R^9$, $R^{10}$, $R^{1d}$, $R^{1e}$, $R^{1f}$ ring B, and n are each as defined herein.

In yet another embodiment, the MDM2 inhibitor provided herein is a compound of Formula (VI):

(VI)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^7$, $R^8$, $R^9$, $R^{10}$, $R^{1d}$, $R^{1e}$, $R^{1f}$, ring B, and n are each as defined herein.

In one embodiment, in Formula (V) or (VI),
ring B is $C_{3-10}$ cycloalkyl or heterocyclyl;
$R^1$ is hydrogen, $C_{1-6}$ alkyl, $C_{3-10}$ cycloalkyl, heterocyclyl, $-NR^{1b}$ or $-OR^{1a}$; and n is an integer of 0, 1, or 2;
$R^2$, $R^4$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or $-OR^{1a}$; or
$R^{1d}$ and $R^{1e}$ together with the carbon to which they are attached form $C_{3-10}$ cycloalkyl or heterocyclyl;
$R^{1f}$ is $-C(=O)OR^{1a}$, $-C(=O)NR^{1b}R^{1c}$, or $-C(=O)NHSO_2CH_3$; and
each $R^a$, $R^{1b}$, and $R^{1c}$ is independently hydrogen or $C_{1-6}$ alkyl;
wherein each alkyl, cycloalkyl, and heterocyclyl is optionally substituted with one or more, in one embodiment, one, two, three, or four, substituents Q.

In another embodiment, in Formula (V) or (VI),
ring B is $C_{3-10}$ cycloalkyl;
$R^1$ is hydrogen or $C_{1-6}$ alkyl; and n is an integer of 0, 1, or 2;
$R^2$, $R^4$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or $-OR^{1a}$;
$R^{1f}$ is $-C(=O)OR^{1a}$, $-C(=O)NR^{1b}R^{1c}$ or $-C(=O)NHSO_2CH_3$; and
each $R^{1a}$, $R^{1b}$, and $R^{1c}$ is independently hydrogen or $C_{1-6}$ alkyl;
wherein each alkyl is independently substituted with one or more, in one embodiment, one, two, three, or four, substituents Q.

In yet another embodiment, in Formula (V) or (VI),
ring B is cyclohexyl or cyclobutyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;
$R^7$ is fluoro;
$R^{1d}$ and $R^{1e}$ are each independently hydrogen, fluoro, methyl, or hydroxy; and
$R^{1f}$ is $-C(=O)OH$, $-C(=O)NH_2$, or $-C(=O)NHSO_2CH_3$.

In still another embodiment, in Formula (V) or (VI), ring B together with $R^{1d}$ and $R^{1e}$ is 3,3-dimethylcyclobutyl, cyclohexyl, 4,4-difluorocyclohexyl, or 4-hydroxy-4-methylcyclohexyl;
$R^1$ is hydrogen, methyl, or ethyl; and n is an integer of 0;
$R^2$, $R^4$, $R^5$, $R^8$, $R^9$, and $R^{10}$ are each hydrogen;
$R^3$ is chloro;
$R^7$ is fluoro; and
$R^{1f}$ is $-C(=O)OH$, $-C(=O)NH_2$, or $-C(=O)NHSO_2CH_3$.

In yet another embodiment, the MDM2 inhibitor provided herein is a compound of Formula (VII):

(VII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, $R^7$, $R^8$, $R^9$, $R^{10}$, $R^{1d}$, $R^{1e}$, ring B, and n are each as defined herein.

In one embodiment, in Formula (VII),
ring B is $C_{3-10}$ cycloalkyl or heterocyclyl;
$R^1$ is hydrogen, $C_{1-6}$ alkyl, $C_{3-10}$ cycloalkyl, heterocyclyl, or $OR^{1a}$; and n is an integer of 0, 1, or 2;
$R^2$, $R^5$, $R^8$, $R^9$, and $R^{10}$ are each independently hydrogen, fluoro, chloro, methyl, or trifluoromethyl;
$R^3$ is chloro;
$R^6$ is

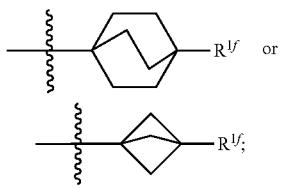

wherein each $R^{1f}$ is independently —C(=O)$OR^{1a}$, —C(=O)$NR^{1b}R^{1c}$, or —C(=O)NHSO$_2$CH$_3$;
$R^7$ is fluoro;
$R^{1d}$ and $R^{1e}$ are each independently hydrogen, halo, $C_{1-6}$ alkyl, or —$OR^{1a}$; or $R^{1d}$ and $R^{1e}$ together with the carbon to which they are attached form $C_{3-10}$ cycloalkyl or heterocyclyl; and
each $R^{1a}$, $R^{1b}$, and $R^{1c}$ is independently hydrogen or $C_{1-6}$ alkyl;
wherein each alkyl, cycloalkyl, and heterocyclyl is optionally substituted with one or more, in one embodiment, one, two, three, or four, substituents Q.

In another embodiment, in Formula (VII),
ring B is $C_{3-10}$ cycloalkyl;
$R^1$ is hydrogen or $C_{1-6}$ alkyl; and n is an integer of 0, 1, or 2;
$R^2$, $R^5$, $R^8$, $R^9$, and $R^{10}$ are each independently hydrogen, fluoro, chloro, methyl, or trifluoromethyl;
$R^3$ is chloro;
$R^6$ is

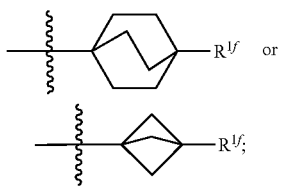

wherein each $R^{1f}$ is independently —C(=O)$OR^{1a}$, —C(=O)$NR^{1b}R^{1c}$, or —C(=O)NHSO$_2$CH$_3$;
$R^7$ is fluoro;
$R^{1d}$ and $R^{1e}$ are each independently hydrogen, halo, $C_{1-6}$ alkyl, or —$OR^{1a}$; and
each $R^{1a}$, $R^{1b}$, and $R^{1c}$ is independently hydrogen or $C_{1-6}$ alkyl;
wherein each alkyl is independently substituted with one or more, in one embodiment, one, two, three, or four, substituents Q.

In yet another embodiment, in Formula (VII),
ring B is cyclohexyl or cyclobutyl;
$R^1$ is hydrogen, methyl, or ethyl; and n is an integer of 0;

$R^2$, $R^5$, $R^8$, $R^9$, and $R^{10}$ are each hydrogen;
$R^3$ is chloro;
$R^6$ is

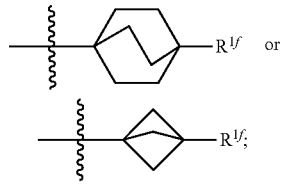

wherein each $R^{1f}$ is independently —C(=O)OH, —C(=O)NH$_2$, or —C(=O)NHSO$_2$CH$_3$;
$R^7$ is fluoro; and
$R^{1d}$ and $R^{1e}$ are each independently hydrogen, fluoro, methyl, or hydroxy.

In still another embodiment, in Formula (VII),
ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;
$R^1$ is hydrogen, methyl, or ethyl; and n is an integer of 0;
$R^2$, $R^5$, $R^8$, $R^9$, and $R^{10}$ are each hydrogen;
$R^3$ is chloro;
$R^6$ is

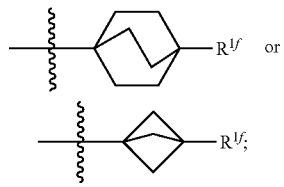

wherein each $R^{1f}$ is independently —C(=O)OH, —C(=O)NH$_2$, or —C(=O)NHSO$_2$CH$_3$; and
$R^7$ is fluoro.

In yet another embodiment, the MDM2 inhibitor provided herein is a compound of Formula (VIII):

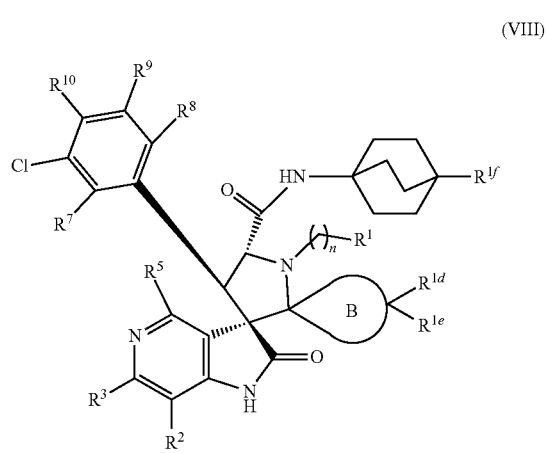

(VIII)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^7$, $R^8$, $R^9$, $R^{10}$, $R^{1d}$, $R^{1e}$, $R^{1f}$, ring B, and n are each as defined herein.

In still another embodiment, the MDM2 inhibitor provided herein is a compound of Formula (IX):

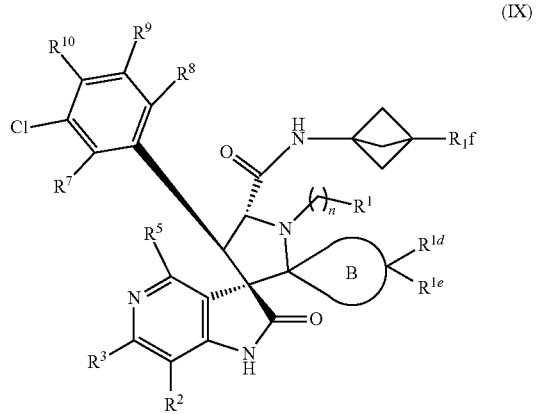

(IX)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^7$, $R^8$, $R^9$, $R^{10}$, $R^{1d}$, $R^{1e}$, ring B, and n are each as defined herein.

In one embodiment, in Formula (VIII) or (IX),
ring B is $C_{3-10}$ cycloalkyl or heterocyclyl;
$R^1$ is hydrogen, $C_{1-6}$ alkyl, $C_{3-10}$ cycloalkyl, heterocyclyl, $-NR^{1b}R^{1c}$, or $-OR^{1a}$; and n is an integer of 0, 1, or 2;
$R^2$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or $-OR^{1a}$; or $R^{1d}$ and $R^{1e}$ together with the carbon to which they are attached form $C_{3-10}$ cycloalkyl or heterocyclyl;
$R^{1f}$ is $-C(=O)OR^{1a}$, $-C(=O)NR^{1b}R^{1c}$, or $-C(=O)NHSO_2CH_3$; and
each $R^{1a}$, $R^{1b}$, and $R^{1c}$ is independently hydrogen or $C_{1-6}$ alkyl;
wherein each alkyl, cycloalkyl, and heterocyclyl is optionally substituted with one or more, in one embodiment, one, two, three, or four, substituents Q.

In another embodiment, in Formula (VIII) or (IX),
ring B is $C_{3-10}$ cycloalkyl;
$R^1$ is hydrogen or $C_{1-6}$ alkyl; and n is an integer of 0, 1, or 2;
$R^2$, $R^5$, $R^8$, $R^9$, and $R^{10}$ are each independently hydrogen, fluoro, chloro, methyl, or trifluoromethyl;
$R^3$ is chloro;
$R^7$ is fluoro;
$R^{1d}$ and $R^{1e}$ are each independently hydrogen, halo, $C_{1-6}$ alkyl, or $-OR^{1a}$;
$R^{1f}$ is $-C(=O)OR^{1a}$, $-C(=O)NR^{1b}R^{1c}$, or $-C(=O)NHSO_2CH_3$; and
each $R^{1a}$, $R^{1b}$, and $R^{1c}$ is independently hydrogen or $C_{1-6}$ alkyl;
wherein each alkyl is independently substituted with one or more, in one embodiment, one, two, three, or four, substituents Q.

In yet another embodiment, in Formula (VIII) or (IX),
ring B is cyclohexyl or cyclobutyl;
$R^1$ is hydrogen, methyl, or ethyl; and n is an integer of 0;
$R^2$, $R^5$, $R^8$, $R^9$, and $R^{10}$ are each hydrogen;
$R^3$ is chloro;
$R^7$ is fluoro;
$R^{1d}$ and $R^{1e}$ are each independently hydrogen, fluoro, methyl, or hydroxy; and
$R^{1f}$ is $-C(=O)OH$, $-C(=O)NH_2$, or $-C(=O)NHSO_2CH_3$.

In still another embodiment, in Formula (VIII) or (IX),
ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;
$R^1$ is hydrogen, methyl, or ethyl; and n is an integer of 0;
$R^2$, $R^5$, $R^8$, $R^9$, and $R^{10}$ are each hydrogen;
$R^3$ is chloro;
$R^7$ is fluoro; and
$R^{1f}$ is $C(=O)OH$, $-C(=O)NH_2$, or $-C(=O)NHSO_2CH_3$.

The groups, $R^1$, $R^2$, $R^3$, $R^4$, $R^5$, $R^6$, $R^7$, $R^8$, $R^9$, $R^{10}$, $R^{1a}$, $R^{1b}$, $R^{1c}$, $R^{1d}$, $R^{1e}$, $R^{1f}$, ring Ar, ring B, and n, in formulae described herein, including Formulae I to IX, are further defined in the embodiments described herein. All combinations of the embodiments provided herein for such groups are within the scope of this disclosure.

In certain embodiments, $R^1$ is hydrogen. In certain embodiments, $R^1$ is $C_{1-6}$ alkyl, optionally substituted with one or more substituents Q. In certain embodiments, le is methyl or ethyl, each optionally substituted with one or more substituents Q. In certain embodiments, $R^1$ is $C_{3-10}$ cycloalkyl, optionally substituted with one or more substituents Q. In certain embodiments, $R^1$ is heterocyclyl, optionally substituted with one or more substituents Q. In certain embodiments, $R^1$ is $-OR^{1a}$, wherein $R^{1a}$ is as defined herein. In certain embodiments, $R^1$ is $-NR^{1b}R^{1c}$, wherein $R^{1b}$ and $R^{1c}$ are each as defined herein. In certain embodiments, $R^{1a}$ is hydrogen, methyl, or ethyl.

In certain embodiments, $R^2$ is hydrogen. In certain embodiments, $R^2$ is fluoro. In certain embodiments, $R^2$ is chloro. In certain embodiments, $R^2$ is methyl. In certain embodiments, $R^2$ is trifluoromethyl.

In certain embodiments, $R^3$ is hydrogen. In certain embodiments, $R^3$ is fluoro. In certain embodiments, $R^3$ is chloro. In certain embodiments, $R^3$ is methyl. In certain embodiments, $R^3$ is trifluoromethyl.

In certain embodiments, $R^4$ is hydrogen. In certain embodiments, $R^4$ is fluoro. In certain embodiments, $R^4$ is chloro. In certain embodiments, $R^4$ is methyl. In certain embodiments, $R^4$ is trifluoromethyl.

In certain embodiments, $R^5$ is hydrogen. In certain embodiments, $R^5$ is fluoro. In certain embodiments, $R^5$ is chloro. In certain embodiments, $R^5$ is methyl. In certain embodiments, $R^5$ is trifluoromethyl.

In certain embodiments, $R^6$ is

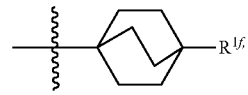

wherein $R^{1f}$ is as defined herein. In certain embodiments, $R^6$ is

[structure: bicyclo[2.2.2]octane with CO₂H]

In certain embodiments, $R^6$ is

[structure: bicyclo[2.2.2]octane with C(O)NH₂]

In certain embodiments, $R^6$ is

[structure: bicyclo[2.2.2]octane with C(O)NHSO₂CH₃]

In certain embodiments, $R^6$ is

[structure: bicyclo[1.1.1]pentane with $R^{1f}$]

wherein $R^{1f}$ is as defined herein. In certain embodiments, $R^6$ is

[structure: bicyclo[1.1.1]pentane with CO₂H]

In certain embodiments, $R^6$ is

[structure: bicyclo[1.1.1]pentane with C(O)NH₂]

In certain embodiments, $R^6$ is

[structure: bicyclo[1.1.1]pentane with C(O)NHSO₂CH₃]

In certain embodiments, $R^7$ is hydrogen. In certain embodiments, $R^7$ is fluoro. In certain embodiments, $R^7$ is chloro. In certain embodiments, $R^7$ is methyl. In certain embodiments, $R^7$ is trifluoromethyl.

In certain embodiments, $R^8$ is hydrogen. In certain embodiments, $R^8$ is fluoro. In certain embodiments, $R^8$ is chloro. In certain embodiments, $R^8$ is methyl. In certain embodiments, $R^8$ is trifluoromethyl.

In certain embodiments, $R^9$ is hydrogen. In certain embodiments, $R^9$ is fluoro. In certain embodiments, $R^9$ is chloro. In certain embodiments, $R^9$ is methyl. In certain embodiments, $R^9$ is trifluoromethyl.

In certain embodiments, $R^{10}$ is hydrogen. In certain embodiments, $R^{10}$ is fluoro. In certain embodiments, $R^{10}$ is chloro. In certain embodiments, $R^{10}$ is methyl. In certain embodiments, $R^{10}$ is trifluoromethyl.

In certain embodiments, $R^{1a}$ is hydrogen. In certain embodiments, $R^{1a}$ is $C_{1-6}$ alkyl, optionally substituted with one or more substituents Q.

In certain embodiments, $R^{1b}$ is hydrogen. In certain embodiments, $R^{1b}$ is $C_{1-6}$ alkyl, optionally substituted with one or more substituents Q.

In certain embodiments, $R^{1c}$ is hydrogen. In certain embodiments, $R^{1c}$ is $C_{1-6}$ alkyl, optionally substituted with one or more substituents Q.

In certain embodiments, $R^{1d}$ is hydrogen. In certain embodiments, $R^{1d}$ is halo. In certain embodiments, $R^{1d}$ is fluoro. In certain embodiments, $R^{1d}$ is $C_{1-6}$ alkyl, optionally substituted with one or more substituents Q. In certain embodiments, $R^{1d}$ is methyl, optionally substituted with one or more substituents Q. In certain embodiments, $R^{1d}$ is —$OR^{1a}$, wherein $R^{1a}$ is as defined herein. In certain embodiments, $R^{1d}$ is —OH. In certain embodiments, $R^{1d}$ is hydrogen, fluoro, methyl, or hydroxy.

In certain embodiments, $R^{1e}$ is hydrogen. In certain embodiments, $R^{1e}$ is halo. In certain embodiments, $R^{1e}$ is fluoro. In certain embodiments, $R^{1e}$ is $C_{1-6}$ alkyl, optionally substituted with one or more substituents Q. In certain embodiments, $R^{1e}$ is methyl, optionally substituted with one or more substituents Q. In certain embodiments, $R^{1e}$ is —$OR^{1a}$, wherein $R^{1a}$ is as defined herein. In certain embodiments, $R^{1e}$ is —OH. In certain embodiments, $R^{1e}$ is hydrogen, fluoro, methyl, or hydroxy.

In certain embodiments, $R^{1d}$ and $R^{1e}$ together with the carbon to which they are attached form $C_{3-10}$ cycloalkyl, optionally substituted with one or more substituents Q. In certain embodiments, $R^{1d}$ and $R^{1e}$ together with the carbon to which they are attached form heterocyclyl, optionally substituted with one or more substituents Q.

In certain embodiments, $R^{1f}$ is —C(=O)$OR^{1a}$, wherein $R^{1a}$ is as defined herein. In certain embodiments, $R^{1f}$ is —C(=O)OH. In certain embodiments, $R^{1f}$ is —C(=O)$NR^{1b}R^{1c}$, wherein $R^{1b}$ and $R^{1c}$ are each as defined herein. In certain embodiments, $R^{1f}$ is —C(=O)NH₂. In certain embodiments, $R^{1f}$ is —C(=O)NHSO₂CH₃.

In certain embodiments, ring Ar is

[structure: benzene ring with R⁴, R⁵, R³, R² substituents and two * attachment points]

wherein $R^2$, $R^3$, $R^4$, and $R^5$ are each as defined herein. In certain embodiments, ring Ar is

[structure: benzene ring with Cl and two * attachment points]

In certain embodiments, ring Ar is

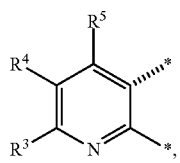

wherein $R^3$, $R^4$, and $R^5$ are each as defined herein. In certain embodiments, ring Ar is

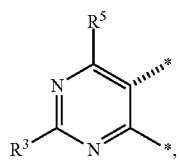

wherein $R^3$ and $R^5$ are each as defined herein.
In certain embodiments, ring Ar is

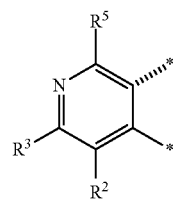

wherein $R^2$, $R^3$, and $R^5$ are each as defined herein. In certain embodiments, ring Ar is

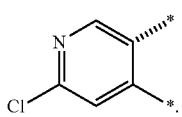

In certain embodiments, ring Ar is

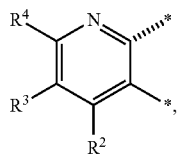

wherein $R^2$, $R^3$, and $R^4$ are each as defined herein.

In certain embodiments, ring B is $C_{3-10}$ cycloalkyl, optionally substituted with one or more substituents Q. In certain embodiments, ring B is cyclobutyl or cyclohexyl, each optionally substituted with one or more substituents Q. In certain embodiments, ring B is cyclobutyl or cyclohexyl, each optionally substituted with one or two $C_{1-6}$ alkyl. In certain embodiments, ring B is cyclobutyl or cyclohexyl, each optionally substituted with one or two methyl. In certain embodiments, ring B is heterocyclyl, optionally substituted with one or more substituents Q.

In certain embodiments, n is an integer of 0. In certain embodiments, n is an integer of 1. In certain embodiments, n is an integer of 2.

In one embodiment, the MDM2 inhibitor provided herein is:

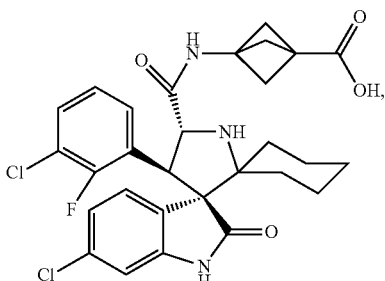
A1

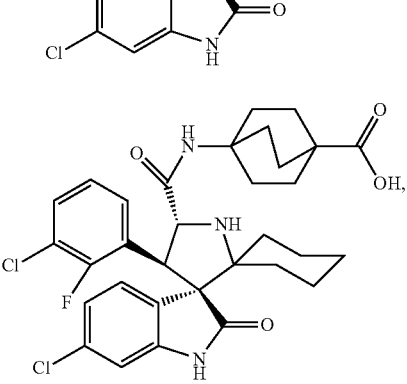
A2

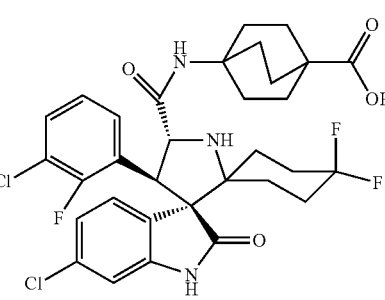
A3

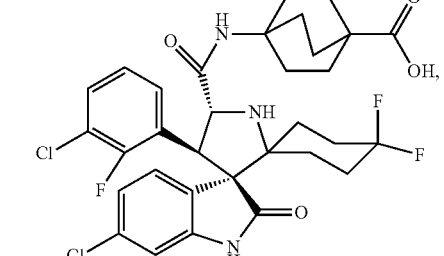
A4

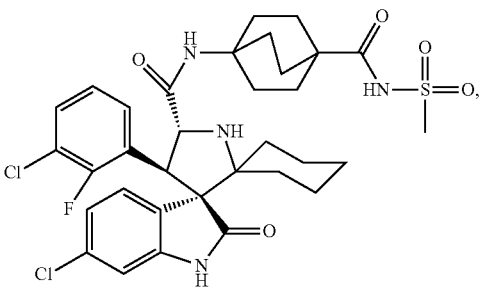
A5

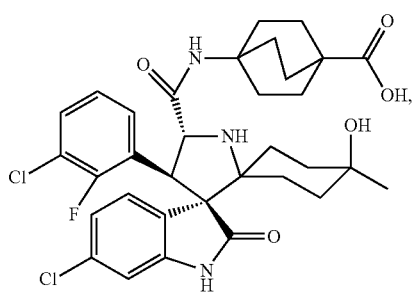

A6

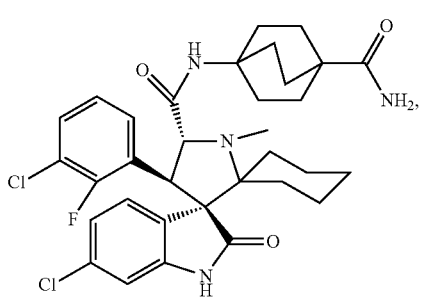

A7

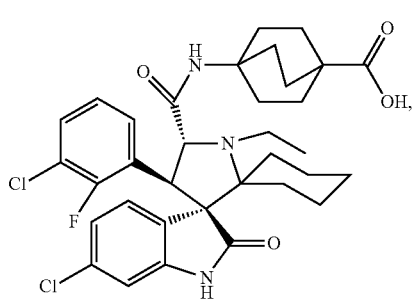

A8

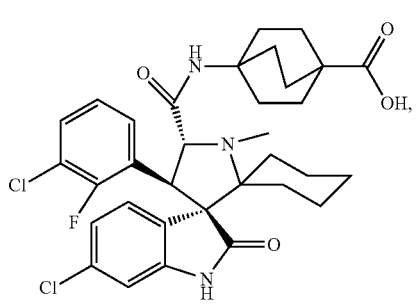

A9

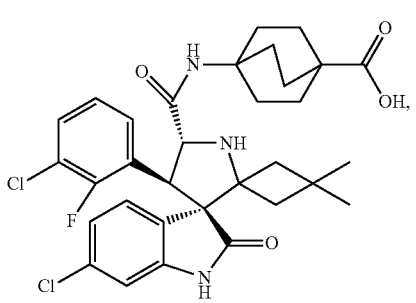

A10

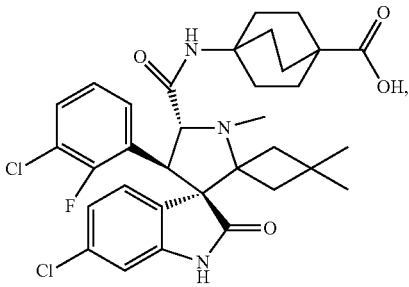

A11

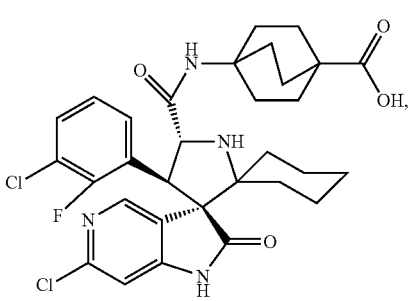

A12

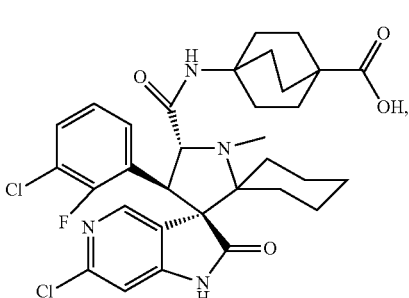

A13

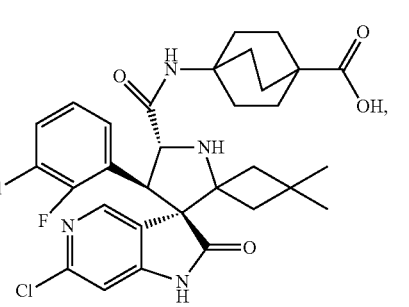

A14

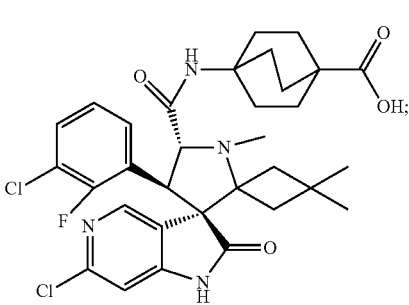

A15 or a tautomer, a mixture of two or more tautomers, or an isotopic variant thereof; or a pharmaceutically acceptable salt, solvate, hydrate, or prodrug thereof.

In one embodiment, the MDM2 inhibitor provided herein is 3-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)bicyclo[1.1.1]pentane-1-carboxylic acid A1, or a tautomer, a mixture of two or more tautomers, or an isotopic variant thereof; or a pharmaceutically acceptable salt, solvate, or hydrate thereof.

In another embodiment, the MDM2 inhibitor provided herein is 4-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)bicyclo[2.2.2]octane-1-carboxylic acid A2, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-4,4-difluoro-2"-oxodispiro[cyclo-hexane-1,2'-pyrrolidine-3',3"-indoline]-5'-carboxamido)bicyclo[2.2.2]octane-1-carboxylic acid A3, or a tautomer, a mixture of two or more tautomers, or an isotopic variant thereof or a pharmaceutically acceptable salt, solvate, or hydrate thereof.

In yet another embodiment, the MDM2 inhibitor provided herein is (3'R,4'S,5'R)-6"-chloro-4'-(3-chloro-2-fluorophenyl)-N-(4-((methylsulfonyl)carbamoyl)-bicyclo[2.2.2]octan-1-yl)-2"-oxodispiro[cyclohexane-1,2'-pyrrolidine-3',3"-indoline]-5'-carboxamide A4, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((1r,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A5, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((1s,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A6, or a tautomer, a mixture of two or more tautomers, or an isotopic variant thereof; or a pharmaceutically acceptable salt, solvate, or hydrate thereof.

In yet another embodiment, the MDM2 inhibitor provided herein is (3'R,4'S,5'R)—N-(4-carbamoylbicyclo[2.2.2]octan-1-yl)-6"-chloro-4'-(3-chloro-2-fluorophenyl)-1'-methyl-2"-oxodispiro[cyclohexane-1,2'-pyrrolidine-3',3"-indoline]-5'-carboxamide A7, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1'-methyl-2"-oxodispiro-[cyclohexane-1,2'-pyrrolidine-3',3"-indoline]-5'-carboxamido)bicyclo[2.2.2]octane-1-carboxylic acid A9, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-3,3-dimethyl-2"-oxodispiro[cyclobutane-1,2'-pyrrolidine-3',3"-indoline]-5'-carboxamido)bicyclo[2.2.2]octane-1-carboxylic acid A10, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1',3,3-trimethyl-2"-oxodispiro[cyclobutane-1,2'-pyrrolidine-3',3"-indoline]-5'-carboxamido)bicyclo[2.2.2]octane-1-carboxylic acid A11, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S, 5'R)-6"-chloro-4'-(3-chloro-2-fluorophenyl)-2"-oxo-1",2"-dihydrodispiro [cyclohexane-1,2'-pyrrolidine-3',3"-pyrrolo[3,2-c]pyridine]-5'-carboxamido) bicyclo[2.2.2]octane-1-carboxylic acid A12, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S, 5'R)-6"-chloro-4'-(3-chloro-2-fluorophenyl)-1'-methyl-2"-oxo-1',2"-dihydrodispiro [cyclohexane-1,2'-pyrrolidine-3',3"-pyrrolo[3,2-c]pyridine]-5'-carboxamido)bicyclo [2.2.2]octane-1-carboxylic acid A13, or a tautomer, a mixture of two or more tautomers, or an isotopic variant thereof or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-3,3-dimethyl-2"-oxo-1",2"-dihydrodispiro [cyclobutane-1,2'-pyrrolidine-3',3"-pyrrolo[3,2-c]pyridine]-5'-carboxamido)bicyclo[2.2.2]octane-1-carboxylic acid A14, or a tautomer, a mixture of two or more tautomers, or an isotopic variant thereof or a pharmaceutically acceptable salt, solvate, or hydrate thereof.

In still another embodiment, the MDM2 inhibitor provided herein is 4-((3'R,4'S,5'R)-6"-chloro-4'-(3-chloro-2-fluorophenyl)-1',3,3-trimethyl-2"-oxo-1",2"-dihydrodispiro [cyclobutane-1,2'-pyrrolidine-3',3"-pyrrolo[3,2-c]pyridine]-5'-carboxamido)bicyclo[2.2.2]octane-1-carboxylic acid A15, or a tautomer, a mixture of two or more tautomers, or an isotopic variant thereof or a pharmaceutically acceptable salt, solvate, or hydrate thereof.

Additional MDM2 inhibitors can be found in U.S. Pat. No. 9,745,314, the disclosure of which is incorporated herein by reference in its entirety.

In certain embodiments, the MDM2 inhibitor provided herein is deuterium-enriched. In certain embodiments, the MDM2 inhibitor provided herein is carbon-13 enriched. In certain embodiments, the MDM2 inhibitor provided herein is carbon-14 enriched. In certain embodiments, the MDM2 inhibitor provided herein contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, the MDM2 inhibitor provided herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, the MDM2 inhibitor provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the MDM2 inhibitor provided herein has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the MDM2 inhibitor provided herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the MDM2 inhibitor provided herein is no less than the natural abundance of the isotope specified.

In certain embodiments, at least one of the atoms of the MDM2 inhibitor provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the MDM2 inhibitor provided herein, as specified as $^{13}$C-enriched, has carbon-13 enrichment of no less than about 2%, no less than about 5%, no less than about 10%, no less than about 20%, no less than about 50%, no less than about 70%, no less than about 80%, no less than about 90%, or no less than about 98%.

In certain embodiments, the MDM2 inhibitor provided herein is isolated or purified. In certain embodiments, the MDM2 inhibitor provided herein has a purity of at least about 80%, at least about 90%, at least about 95%, at least about 98%, at least about 99%, or at least about 99.5% by weight.

The MDM2 inhibitor provided herein is intended to encompass all possible stereoisomers, unless a particular stereochemistry is specified. Where the MDM2 inhibitor contains an alkenyl group, it may exist as one or mixture of geometric cis/trans (or Z/E) isomers. Where structural isomers are interconvertible, it may exist as a single tautomer or a mixture of tautomers. This can take the form of proton tautomerism in the MDM2 inhibitor that contains, for example, an imino, keto, or oxime group; or so-called valence tautomerism in the MDM2 inhibitor that contain an aromatic moiety. It follows that a single MDM2 inhibitor may exhibit more than one type of isomerism.

The MDM2 inhibitor provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the MDM2 inhibitor provided herein contains an acidic or basic moiety, it can also be provided as a pharmaceutically acceptable salt. See, e.g., Berge et al., *J. Pharm. Sci.* 1977, 66, 1-19; *Handbook of Pharmaceutical Salts: Properties, Selection, and Use*, 2nd ed.; Stahl and Wermuth Eds.; Wiley-VCH and VHCA, Zurich, 2011. In certain embodiments, a pharmaceutically acceptable salt of the MDM2 inhibitor provided herein is a solvate. In certain embodiments, a pharmaceutically acceptable salt of the MDM2 inhibitor provided herein is a hydrate.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The MDM2 inhibitor provided herein may also be provided as a prodrug, which is a functional derivative of a compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, e.g., Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In one embodiment, an MDM2 inhibitor disclosed herein is provided as a pharmaceutical composition comprising the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In one embodiment, the pharmaceutical composition comprises 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8, or a tautomer, a mixture of two or more tautomers, or an isotopic variant thereof; or a pharmaceutically acceptable salt, solvate, or hydrate thereof; and a pharmaceutically acceptable excipient.

The MDM2 inhibitor-containing pharmaceutical composition can be formulated in various dosage forms, including, but not limited to, dosage forms for oral, parenteral, and topical administration. The MDM2 inhibitor-containing pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy,* supra; *Modified-Release Drug Delivery Technology,* 2nd Edition, Rathbone et al., Eds., Marcel Dekker, Inc.: New York, NY, 2008.

In one embodiment, the MDM2 inhibitor-containing pharmaceutical composition is formulated in a dosage form for oral administration. In another embodiment, MDM2 inhibitor-containing pharmaceutical composition is formulated as a tablet, capsule, or solution for oral administration. In yet another embodiment, the MDM2 inhibitor-containing pharmaceutical composition is formulated as a tablet. In yet another embodiment, the MDM2 inhibitor-containing pharmaceutical composition is formulated as a capsule. In yet another embodiment, the MDM2 inhibitor-containing pharmaceutical composition is formulated as a solution. In yet another embodiment, the MDM2 inhibitor-containing pharmaceutical composition is formulated in a dosage form for parenteral administration. In yet another embodiment, the MDM2 inhibitor-containing pharmaceutical composition is formulated in a dosage form for intravenous administration. In yet another embodiment, the MDM2 inhibitor-containing pharmaceutical composition is formulated in a dosage form for intramuscular administration. In yet another embodiment, the MDM2 inhibitor-containing pharmaceutical composition is formulated in a dosage form for subcutaneous administration. In still another embodiment, the MDM2 inhibitor-containing pharmaceutical composition is formulated in a dosage form for topical administration.

The MDM2 inhibitor-containing pharmaceutical composition can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The MDM2 inhibitor-containing pharmaceutical composition can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the MDM2 inhibitor-containing pharmaceutical composition.

Platinum Compounds

In one embodiment, the platinum compound provided herein is an antineoplastic compound. In another embodiment, the platinum compound provided herein is carboplatin, cisplatin, ethacraplatin, heptaplatin, iproplatin, lobaplatin, mitaplatin, nedaplatin, ormaplatin, oxaliplatin, phenanthriplatin, picoplatin, pyriplatin, satrplatin, or triplatin tetranitrate. In yet another embodiment, the platinum compound provided herein is carboplatin, cisplatin, heptaplatin, lobaplatin, nedaplatin, or oxaliplatin. In still another embodiment, the platinum compound in the method provided herein is carboplatin, cisplatin, nedaplatin, or oxaliplatin.

In one embodiment, the platinum compound provided herein is carboplatin. In another embodiment, the platinum compound provided herein is cisplatin. In yet another embodiment, the platinum compound provided herein is ethacraplatin. In yet another embodiment, the platinum compound provided herein is heptaplatin. In yet another embodiment, the platinum compound provided herein is iproplatin. In yet another embodiment, the platinum compound provided herein is lobaplatin. In yet another embodiment, the platinum compound provided herein is mitaplatin. In yet another embodiment, the platinum compound provided herein is nedaplatin. In yet another embodiment, the platinum compound provided herein is ormaplatin. In yet another embodiment, the platinum compound provided herein is oxaliplatin. In yet another embodiment, the platinum compound provided herein is phenanthriplatin. In yet another embodiment, the platinum compound provided herein is picoplatin. In yet another embodiment, the platinum compound provided herein is pyriplatin. In yet another embodiment, the platinum compound provided herein is satrplatin. In still another embodiment, the platinum compound provided herein is triplatin tetranitrate.

Additional platinum compounds that are suitable for use in a method provided herein are disclosed in Johnstone et al., *Chem. Rev.* 2016, 116, 3436-3486, the disclosure of which is incorporated herein by reference in its entirety.

In one embodiment, a platinum compound disclosed herein is provided as a pharmaceutical composition, comprising the platinum compound and a pharmaceutically acceptable excipient. In one embodiment, the platinum compound-containing pharmaceutical composition comprises the platinum compound and water.

The platinum compound-containing pharmaceutical composition can be formulated in various dosage forms, including dosage forms for oral, parenteral, and topical administration. The platinum compound-containing pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy*, supra; *Modified-Release Drug Delivery Technology*, 2nd Edition, Rathbone et al., Eds., Marcel Dekker, Inc.: New York, NY, 2008.

In one embodiment, the platinum compound-containing pharmaceutical composition is formulated in a dosage form for parenteral administration. In another embodiment, the platinum compound-containing pharmaceutical composition is formulated in a dosage form for intravenous administration. In yet another embodiment, the platinum compound-containing pharmaceutical composition is formulated in a dosage form for intramuscular administration. In still another embodiment, the platinum compound-containing pharmaceutical composition is formulated in a dosage form for subcutaneous administration.

The platinum compound-containing pharmaceutical composition can be provided in a unit-dosage form or multiple-dosage form.

The platinum compound-containing pharmaceutical composition can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the platinum compound-containing pharmaceutical composition.

Methods of Use

In one embodiment, provided herein is a method of treating, preventing, or alleviating a disorder, disease, or condition mediated by an MDM2 in a subject, comprising administering to the subject (i) an MDM2 inhibitor provided herein, e.g., a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) a platinum compound provided herein. In one embodiment, the disorder, disease, or condition mediated by an MDM2 is cancer.

In another embodiment, provided herein is a method of treating, preventing, or alleviating a disorder, disease, or condition mediated by an MDM2/p53 interaction in a subject, comprising administering to the subject (i) an MDM2 inhibitor provided herein, e.g., a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) a platinum compound provided herein. In one embodiment, the disorder, disease, or condition mediated by an MDM2/p53 interaction is cancer.

In one embodiment, the MDM2 is a human MDM2, which is also known as HDM2.

In yet another embodiment, provided herein is a method of treating, preventing, or alleviating cancer in a subject, comprising administering to the subject (i) an MDM2 inhibitor provided herein, e.g., a compound of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) a platinum compound provided herein.

In one embodiment, the cancer is solid cancer. In another embodiment, the cancer is salivary gland cancer. In yet another embodiment, the salivary gland cancer is stage I, stage II, stage III, or stage IV salivary gland cancer. In still another embodiment, the salivary gland cancer is stage VIA, stage VIB, or stage VIC salivary gland cancer.

In one embodiment, the salivary gland cancer is acinic cell carcinoma, adenoid cystic carcinoma, adenocarcinoma NOS, mucoepidermoid carcinoma, or polymorphous adenocarcinoma. In another embodiment, the salivary gland cancer is adenosquamous carcinoma, basal cell adenocarcinoma, carcinoma ex pleomorphic adenoma, carcinosarcoma, clear cell carcinoma, cystadenocarcinoma, epithelial-myoepithelial carcinoma, lymphoepithelial carcinoma, myoepithelial carcinoma, oncocytic carcinoma, poorly differentiated carcinoma, salivary duct carcinoma, sebaceous adenocarcinoma, secretory carcinoma, or squamous cell carcinoma. In yet another embodiment, the salivary gland cancer is mucoepidermoid carcinoma, adenoid cystic carcinoma, acinic cell carcinoma, carcinoma ex pleomorphic adenoma, squamous cell carcinoma, or adenocarcinoma. In still another embodiment, the salivary gland cancer is mucoepidermoid carcinoma, acinic cell carcinoma, polymorphous adenocarcinoma, or epithelial-myoepithelial carcinoma.

In certain embodiments, the cancer is metastatic. In certain embodiments, the cancer is refractory. In certain embodiments, the cancer is relapsed. In certain embodiments, the cancer is drug-resistant. In certain embodiments, the cancer is multidrug-resistant. In certain embodiments, the cancer is resistant to carboplatin, cisplatin, cyclophosphamide, docetaxel, doxorubicin, 5-fluorouracil, methotrexate, paclitaxel, or vinorelbine.

In one embodiment, the cancer has a non-pathogenic p53. In another embodiment, the cancer has a functional p53. In yet another embodiment, the cancer has a wild-type p53. In yet another embodiment, the cancer does not have a pathogenic p53. In still another embodiment, the cancer does not have a non-functional p53.

The functional status of p53 can be determined using conventional methods known to one of ordinary skill in the art. See, e.g., Jordan et al., *Mol. Cancer Res.* 2010, 8, 701-716; Robles & Harris, *Cold Spring Harb. Perspect. Med.* 2010, 2, a001016.

In certain embodiments, the subject is a mammal. In certain embodiments, the subject is a human.

The methods provided herein encompass treating a subject regardless of patient's age, although some diseases or disorders are more common in certain age groups.

In certain embodiments, the subject to be treated with a method provided herein has not been treated with an anticancer therapy for the cancer to be treated. In certain embodiments, the subject to be treated with a method provided herein has not been treated with an MDM2 inhibitor for the cancer to be treated. In certain embodiments, the subject to be treated with a method provided herein has not been treated with an MDM2 inhibitor provided herein for the cancer to be treated.

In certain embodiments, the subject to be treated with a method provided herein has been treated with an anticancer therapy for the cancer to be treated. In certain embodiments, the subject to be treated with a method provided herein has been treated with an MDM2 inhibitor for the cancer to be treated. In certain embodiments, the subject to be treated with a method provided herein has been treated with an MDM2 inhibitor provided herein for the cancer to be treated.

In certain embodiments, the therapeutically effective amount of an MDM2 inhibitor provided herein is ranging from about 0.1 mg/kg every other day to about 10 mg/kg per day, from about 0.2 mg/kg every other day to about 5 mg/kg per day, or from about 0.5 mg/kg every other day to about 5 mg/kg per day. In one embodiment, the therapeutically effective amount of an MDM2 inhibitor provided herein is ranging from about 0.1 mg/kg every other day to about 10 mg/kg per day. In another embodiment, the therapeutically effective amount of an MDM2 inhibitor provided herein is ranging from about 0.2 mg/kg every other day to about 5 mg/kg per day. In yet another embodiment, the therapeutically effective amount of an MDM2 inhibitor provided herein is ranging from about 0.5 mg/kg every other day to about 5 mg/kg per day.

In certain embodiments, the therapeutically effective amount of an MDM2 inhibitor provided herein is ranging from about 0.1 to about 10 mg/kg per day, from about 0.2 to about 5 mg/kg per day, or from about 0.5 to about 5 mg/kg per day. In one embodiment, the therapeutically effective amount of an MDM2 inhibitor provided herein is ranging from about 0.1 to about 10 mg/kg per day. In another embodiment, the therapeutically effective amount of an MDM2 inhibitor provided herein is ranging from about 0.2 to about 5 mg/kg per day. In yet another embodiment, the therapeutically effective amount of an MDM2 inhibitor provided herein is ranging from about 0.5 to about 5 mg/kg per day. In still another embodiment, the therapeutically effective amount of an MDM2 inhibitor provided herein is ranging from about 0.5, about 0.6, about 0.7, about 0.8, about 0.9, about 1, about 1.2, about 1.3, about 1.4, about 1.5, about 1.6, about 1.7, about 1.8, about 1.9, about 2, about 2.1, about 2.2, about 2.3, about 2.4, or about 2.5 mg/kg per day.

In certain embodiments, the therapeutically effective amount of an MDM2 inhibitor provided herein is ranging from about 0.1 to about 10 mg/kg every other day, from about 0.2 to about 5 mg/kg every other day, or from about 0.5 to about 5 mg/kg every other day. In one embodiment, the therapeutically effective amount of an MDM2 inhibitor provided herein is ranging from about 0.1 to about 10 mg/kg every other day. In another embodiment, the therapeutically effective amount of an MDM2 inhibitor provided herein is ranging from about 0.2 to about 5 mg/kg every other day. In yet another embodiment, the therapeutically effective amount of an MDM2 inhibitor provided herein is ranging from about 0.5 to about 5 mg/kg every other day. In still another embodiment, the therapeutically effective amount of an MDM2 inhibitor provided herein is ranging from about 0.5, about 0.6, about 0.7, about 0.8, about 0.9, about 1, about 1.2, about 1.3, about 1.4, about 1.5, about 1.6, about 1.7, about 1.8, about 1.9, about 2, about 2.1, about 2.2, about 2.3, about 2.4, or about 2.5 mg/kg every other day.

In certain embodiments, the therapeutically effective amount of an MDM2 inhibitor provided herein is ranging from about 1 mg every other day to about 1,000 mg per day, from about 2 mg every other day to about 500 mg per day, from about 5 mg every other day to about 250 mg per day, or from about 10 mg every other day to about 200 mg per day. In one embodiment, the therapeutically effective amount of an MDM2 inhibitor provided herein is ranging from about 1 mg every other day to about 1,000 mg per day. In another embodiment, the therapeutically effective amount of an MDM2 inhibitor provided herein is ranging from about 2 mg every other day to about 500 mg per day. In yet another embodiment, the therapeutically effective amount of an MDM2 inhibitor provided herein is ranging from about 5 mg every other day to about 250 mg per day. In yet another embodiment, the therapeutically effective amount of an MDM2 inhibitor provided herein is ranging from about 10 mg every other day to about 200 mg per day.

In certain embodiments, the therapeutically effective amount of an MDM2 inhibitor provided herein is ranging from about 1 to about 1,000 mg per day, from about 2 to about 500 mg per day, from about 5 to about 250 mg per day, or from about 10 to about 200 mg per day. In one embodiment, the therapeutically effective amount of an MDM2 inhibitor provided herein is ranging from about 1 to about 1,000 mg per day. In another embodiment, the therapeutically effective amount of an MDM2 inhibitor provided herein is ranging from about 2 to about 500 mg per day. In yet another embodiment, the therapeutically effective amount of an MDM2 inhibitor provided herein is ranging from about 5 to about 250 mg per day. In yet another embodiment, the therapeutically effective amount of an MDM2 inhibitor provided herein is ranging from about 10 to about 200 mg per day. In still another embodiment, the therapeutically effective amount of an MDM2 inhibitor provided herein is ranging from about 10, about 20, about 50, about 60, about 70, about 80, about 90, about 100, about 110, about 120, about 130, about 140, about 150, about 160, about 170, about 180, about 190, or 200 mg per day.

In certain embodiments, the therapeutically effective amount of an MDM2 inhibitor provided herein is ranging from about 1 to about 1,000 mg every other day, from about 2 to about 500 mg every other day, from about 5 to about 250 mg every other day, or from about 10 to about 200 mg every other day. In one embodiment, the therapeutically effective amount of an MDM2 inhibitor provided herein is ranging from about 1 to about 1,000 mg every other day. In another embodiment, the therapeutically effective amount of an MDM2 inhibitor provided herein is ranging from about 2 to about 500 mg every other day. In yet another embodiment, the therapeutically effective amount of an MDM2 inhibitor provided herein is ranging from about 5 to about 250 mg every other day. In yet another embodiment, the therapeutically effective amount of an MDM2 inhibitor provided herein is ranging from about 10 to about 200 mg every other day. In still another embodiment, the therapeutically effective amount of an MDM2 inhibitor provided herein is ranging from about 10, about 20, about 50, about 60, about 70, about 80, about 90, about 100, about 110, about 120, about 130, about 140, about 150, about 160, about 170, about 180, about 190, or 200 mg every other day.

It is understood that the administered dose can also be expressed in units other than mg/kg every other day. For example, doses for parenteral administration can be expressed as mg/m$^2$ every other day. One of ordinary skill in the art would readily know how to convert doses from mg/kg every other day to mg/m$^2$ every other day to given either the height or weight of a subject or both. For example, a dose of 1 mg/m$^2$ every other day for a 65 kg human is approximately equal to 58 mg/kg every other day.

Depending on the disease to be treated and the subject's condition, an MDM2 inhibitor provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration.

In one embodiment, an MDM2 inhibitor provided herein is administered orally. In another embodiment, an MDM2 inhibitor provided herein is administered parenterally. In yet another embodiment, an MDM2 inhibitor is administered intravenously. In yet another embodiment, an MDM2 inhibitor provided herein is administered intramuscularly. In yet another embodiment, an MDM2 inhibitor provided herein is administered subcutaneously. In still another embodiment, an MDM2 inhibitor provided herein is administered topically.

An MDM2 inhibitor provided herein can be delivered as a single dose such as, e.g., a single bolus injection, or oral tablets or pills; or over time such as, e.g., continuous infusion over time or divided bolus doses over time. An MDM2 inhibitor provided herein can be administered repetitively if necessary, for example, until the subject experiences stable disease or regression, or until the subject experiences disease progression or unacceptable toxicity. Stable disease or lack thereof is determined by methods known in the art such as evaluation of subject's symptoms, physical examination, visualization of the cancer that has been imaged using X-ray, CAT, PET, or MM scan and other commonly accepted evaluation modalities.

An MDM2 inhibitor provided herein can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of an MDM2 inhibitor provided herein is administration for one to six days per week, administration in cycles (e.g., daily administration for two to eight consecutive weeks, then a rest period with no administration for up to one week), or administration on alternate days.

It will be understood, however, that the specific dose level and frequency of dosage for any particular subject can be varied and will depend upon a variety of factors including the activity of the specific MDM2 inhibitor employed, the metabolic stability and length of action of that MDM2 inhibitor, the age, body weight, general health, sex, diet, mode and time of administration, rate of excretion, drug combination, the severity of the particular condition, and the host undergoing therapy.

In certain embodiments, the therapeutically effect amount of a platinum compound provided herein is ranging from about 1 mg/m$^2$ every four weeks to 1,000 mg/m$^2$ every week, from about 10 mg/m$^2$ every four weeks to 500 mg/m$^2$ every week, or from about 20 mg/m$^2$ every four weeks to 200 mg/m$^2$ every week. In certain embodiments, the therapeutically effect amount of a platinum compound provided herein is ranging from about 1 mg/m$^2$ every four weeks to 1,000 mg/m$^2$ every week. In certain embodiments, the therapeutically effect amount of a platinum compound provided herein is ranging from about 10 mg/m$^2$ every four weeks to 500 mg/m$^2$ every week. In certain embodiments, the therapeutically effect amount of a platinum compound provided herein is ranging from about 20 mg/m$^2$ every four weeks to 200 mg/m$^2$ every week.

In certain embodiments, the therapeutically effective amount of a platinum compound provided herein is ranging from about 1 to about 500 mg/m$^2$ every week, from about 2 to about 200 mg/m$^2$ every week, from about 5 to about 100 mg/m$^2$ every week, or from about 10 to about 50 mg/m$^2$ every week. In certain embodiments, the therapeutically effective amount of a platinum compound provided herein is ranging from about 1 to about 500 mg/m$^2$ every week. In certain embodiments, the therapeutically effective amount of a platinum compound provided herein is ranging from about 2 to about 200 mg/m$^2$ every week. In certain embodiments, the therapeutically effective amount of a platinum compound provided herein is ranging from about 5 to about 100 mg/m$^2$ every week. In certain embodiments, the therapeutically effective amount of a platinum compound provided herein is ranging from about 10 to about 50 mg/m$^2$ every week.

In certain embodiments, the therapeutically effective amount of a platinum compound provided herein is ranging from about 1 to about 500 mg/m$^2$ every two weeks, from about 2 to about 200 mg/m$^2$ every two weeks, from about 5 to about 100 mg/m$^2$ every two weeks, from about 20 to about 100 mg/m$^2$ every two weeks, from about 50 to about 100 mg/m$^2$ every two weeks, or from about 10 to about 50 mg/m$^2$ every two weeks. In certain embodiments, the therapeutically effective amount of a platinum compound provided herein is ranging from about 1 to about 500 mg/m$^2$ every two weeks. In certain embodiments, the therapeutically effective amount of a platinum compound provided herein is ranging from about 2 to about 200 mg/m$^2$ every two weeks. In certain embodiments, the therapeutically effective amount of a platinum compound provided herein is ranging from about 5 to about 100 mg/m$^2$ every two weeks. In certain embodiments, the therapeutically effective amount of a platinum compound provided herein is ranging from about 20 to about 100 mg/m² every two weeks. In certain embodiments, the therapeutically effective amount of a platinum compound provided herein is ranging from about 50 to about 100 mg/m² every two weeks. In certain embodiments, the therapeutically effective amount of a platinum compound provided herein is ranging from about 10 to about 50 mg/m² every two weeks. In certain embodiments, the therapeutically effective amount of a platinum compound provided herein is about 50, about 55, about 60, about 65, about 70, about 75, about 80, about 85, about 90, about 95, or about 100 mg/m² every two weeks.

In certain embodiments, the therapeutically effective amount of a platinum compound provided herein is ranging from about 10 to about 1,000 mg/m² every three weeks, from about 20 to about 500 mg/m² every three weeks, from about 50 to about 500 mg/m² every three weeks, from about 100 to about 500 mg/m² every three weeks, or from about 50 to about 250 mg/m² every three weeks. In certain embodiments, the therapeutically effective amount of a platinum compound provided herein is ranging from about 10 to about 1,000 mg/m² every three weeks. In certain embodiments, the therapeutically effective amount of a platinum compound provided herein is ranging from about 20 to about 500 mg/m² every three weeks. In certain embodiments, the therapeutically effective amount of a platinum compound provided herein is ranging from about 50 to about 500 mg/m² every three weeks. In certain embodiments, the therapeutically effective amount of a platinum compound provided herein is ranging from about 100 to about 500 mg/m² every three weeks. In certain embodiments, the therapeutically effective amount of a platinum compound provided herein is ranging from about 50 to about 250 mg/m² every three weeks. In certain embodiments, the therapeutically effective amount of a platinum compound provided herein is about 100, about 150, about 200, about 250, about 300, about 350, about 400, about 450, or about 500 mg/m² every three weeks.

In certain embodiments, the therapeutically effective amount of a platinum compound provided herein is ranging from about 10 to about 1,000 mg/m² every four weeks, from about 20 to about 500 mg/m² every four weeks, from about 50 to about 500 mg/m² every four weeks, from about 100 to about 500 mg/m² every four weeks, or from about 50 to about 250 mg/m² every four weeks. In certain embodiments, the therapeutically effective amount of a platinum compound provided herein is ranging from about 10 to about 1,000 mg/m² every four weeks. In certain embodiments, the therapeutically effective amount of a platinum compound provided herein is ranging from about 20 to about 500 mg/m² every four weeks. In certain embodiments, the therapeutically effective amount of a platinum compound provided herein is ranging from about 50 to about 500 mg/m² every four weeks.

In certain embodiments, the therapeutically effective amount of a platinum compound provided herein is ranging from about 100 to about 500 mg/m² every four weeks. In certain embodiments, the therapeutically effective amount of a platinum compound provided herein is ranging from about 50 to about 250 mg/m² every four weeks. In certain embodiments, the therapeutically effective amount of a platinum compound provided herein is about 100, about 150, about 200, about 250, about 300, about 350, about 400, about 450, or about 500 mg/m² every four weeks.

In certain embodiments, a platinum compound provided herein is administered in an amount resulting in an area under a curve (AUC) ranging from about 1 to about 10 mg/mL/min, from about 2 to about 8 mg/mL/min, or from about 4 to about 6 mg/mL/min. In certain embodiments, a platinum compound provided herein is administered in an amount resulting in an AUC ranging from about 1 to about 10 mg/mL/min. In certain embodiments, a platinum compound provided herein is administered in an amount resulting in an AUC ranging from about 2 to about 8 mg/mL/min. In certain embodiments, a platinum compound provided herein is administered in an amount resulting in an AUC ranging from about 4 to about 6 mg/mL/min. In certain embodiments, a platinum compound provided herein is administered in an amount resulting in an AUC of about 4, about 4.5, about 5, about 5.5, or about 6 mg/mL/min.

One way to determine the initial dose of a platinum compound provided herein in order to reach a target AUC is using a mathematical formula known as Calvert formula. This formula takes into account a subject's preexisting renal function or renal function and desired platelet nadir (renal excretion is the major route of elimination for this drug). The initial dose (mg) of the platinum is calculated by multiplying the target AUC with the total of the subject's glomerular filtration rate (GFR) plus 25. See, e.g., van Warmerdam et al., *J. Cancer Res. Clin. Oncol.* 1995, 121, 478-486, the disclosure of which is incorporated herein by reference in its entirety.

In certain embodiments, a platinum compound provided herein is administered parenterally. In certain embodiments, a platinum compound provided herein is administered intramuscularly, intravenously, or subcutaneously. In certain embodiments, a platinum compound provided herein is administered intravenously. In certain embodiments, a platinum compound provided herein is administered via an intravenous infusion.

A platinum compound provided herein can be delivered as a single dose such as, e.g., a single bolus injection; or over time such as, e.g., continuous infusion over time or divided bolus doses over time. A platinum compound provided herein can be administered repetitively if necessary, for example, until the subject experiences stable disease or regression, or until the subject experiences disease progression or unacceptable toxicity. Stable disease or lack thereof is determined by methods known in the art such as evaluation of subject's symptoms, physical examination, visualization of the cancer that has been imaged using X-ray, CAT, PET, or MM scan and other commonly accepted evaluation modalities.

In certain embodiments, a platinum compound provided herein is administered daily, once a week, once every two weeks, once every three weeks, once every four weeks, once a month, or once every two months. In certain embodiments, a platinum compound provided herein is administered daily. In certain embodiments, a platinum compound provided herein is administered once a week. In certain embodiments, a platinum compound provided herein is administered once every two weeks. In certain embodiments, a platinum compound provided herein is administered once every three weeks. In certain embodiments, a platinum compound provided herein is administered once every four weeks. In certain embodiments, a platinum compound provided herein is administered once a month. In certain embodiments, a platinum compound provided herein is administered once every two months.

In certain embodiments, a platinum compound provided herein is administered on Day 1 once a week, once every two weeks, once every three weeks, once every four weeks, once a month, or once every two months. In certain embodiments, a platinum compound provided herein is administered on Day 1 once a week. In certain embodiments, a platinum compound provided herein is administered on Day 1 once every two weeks. In certain embodiments, a platinum compound provided herein is administered on Day 1 once every three weeks. In certain embodiments, a platinum compound provided herein is administered on Day 1 once every four weeks. In certain embodiments, a platinum compound provided herein is administered on Day 1 once a month. In certain embodiments, a platinum compound provided herein is administered on Day 1 once every two months.

It will be understood, however, that the specific dose level and frequency of dosage for any particular subject can be varied and will depend upon a variety of factors including the activity of the specific platinum compound employed, the metabolic stability and length of action of that platinum compound, the age, body weight, general health, sex, diet, mode and time of administration, rate of excretion, drug combination, the severity of the particular condition, and the host undergoing therapy.

In certain embodiments, an MDM2 inhibitor and a platinum compound provided herein are cyclically administered to a subject to be treated. Cycling therapy involves the administration of an MDM2 inhibitor and a platinum compound for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, an MDM2 inhibitor and a platinum compound provided herein are administered for a cycle of about one week, about two weeks, about three weeks, about four weeks, about five weeks, about six weeks, about eight weeks, or about ten weeks, with a rest period of about 1 day to about four weeks. In one embodiment, an MDM2 inhibitor and a platinum compound provided herein are administered for a cycle of three weeks, four weeks, five weeks, or six weeks with a rest period of 1, 3, 5, 7, 9, 12, or 14. In certain embodiments, the rest period is 7 days. In certain embodiments, the rest period is 14 days. In certain embodiments, the rest period is a period that is sufficient for bone marrow recovery. The frequency, number, and length of dosing cycles can be increased or decreased.

In one embodiment, an MDM2 inhibitor and a platinum compound provided herein are administered for two weeks in a 21-day cycle with a 7-day rest period. In another embodiment, an MDM2 inhibitor and a platinum compound provided herein are administered for two weeks in a 21-day cycle with a 7-day rest period, wherein the MDM2 inhibitor is administered every other day and the platinum compound is administered once. In yet another embodiment, an MDM2 inhibitor and a platinum compound provided herein are administered for two weeks in a 21-day cycle with a 7-day rest period, wherein the MDM2 inhibitor is administered on Days 1, 3, 5, 7, 9, 11, and 13; and the platinum compound is administered on Day 1; and wherein the resting period is from Days 15 to 21.

In one embodiment, an MDM2 inhibitor and a platinum compound provided herein are administered for three weeks in a 28-day cycle with a 7-day rest period. In another embodiment, an MDM2 inhibitor and a platinum compound provided herein are administered for three weeks in a 28-day cycle with a 7-day rest period, wherein the MDM2 inhibitor is administered every other day and the platinum compound is administered once. In yet another embodiment, an MDM2 inhibitor and a platinum compound provided herein are administered for three weeks in a 28-day cycle with a 7-day rest period, wherein the MDM2 inhibitor is administered on Days 1, 3, 5, 7, 9, 11, 13, 15, 17, 19, and 21; and the platinum compound is administered on Day 1; and wherein the resting period is from Days 22 to 28.

In one embodiment, an MDM2 inhibitor and a platinum compound provided herein are administered for two weeks in a 21-day cycle with a 7-day rest period, wherein the MDM2 inhibitor is 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; and wherein the platinum compound is carboplatin. In one embodiment, in a 21-day cycle with a 7-day rest period, compound A8 is administered every other day for two weeks and carboplatin is administered once. In another embodiment, in a 21-day cycle with a 7-day rest period, compound A8 is administered on Days 1, 3, 5, 7, 9, 11, and 13; and carboplatin is administered on Day 1.

In one embodiment, an MDM2 inhibitor and a platinum compound provided herein are administered for two weeks in a 28-day cycle with a 7-day rest period, wherein the MDM2 inhibitor is 443'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; and wherein the platinum compound is carboplatin. In one embodiment, in a 28-day cycle with a 7-day rest period, compound A8 is administered every other day for three weeks and carboplatin is administered once. In another embodiment, in a 28-day cycle with a 7-day rest period, compound A8 is administered on Days 1, 3, 5, 7, 9, 11, 13, 15, 17, 19, and 21; and carboplatin is administered on Day 1.

In certain embodiments, the subject is treated with an MDM2 inhibitor and a platinum compound provided herein from about 1 to about 50, from about 2 to about 20, from about 2 to 10, or from about 4 to about 8. In certain embodiments, the subject is treated with an MDM2 inhibitor and a platinum compound provided herein from about 1 to about 50 cycles. In certain embodiments, the subject is treated with an MDM2 inhibitor and a platinum compound provided herein from about 2 to about 20 cycles. In certain embodiments, the subject is treated with an MDM2 inhibitor and a platinum compound provided herein from about 2 to 10 cycles. In certain embodiments, the subject is treated with an MDM2 inhibitor and a platinum compound provided herein from about 4 to about 8 cycles.

In one embodiment, a method provided herein further comprises administering an MDM2 inhibitor provided herein as a single-agent maintenance therapy after the subject has received treatment with an MDM2 inhibitor and a platinum compound. In one embodiment, the subject to receive the single-agent maintenance therapy is responsive to the treatment with an MDM2 inhibitor and a platinum compound. In another embodiment, the subject to receive the single-agent maintenance therapy has a stable disease, partial response, or complete response after receiving the treatment with an MDM2 inhibitor and a platinum compound. In yet another embodiment, the subject to receive the single-agent maintenance therapy has completed from about 1 to about 50 cycles, from about 2 to about 20 cycles, from about 2 to 10 cycles, or from about 4 to about 8 cycles of treatment with an MDM2 inhibitor and a platinum compound.

In certain embodiments, the MDM2 inhibitor as a single-agent maintenance therapy is administered cyclically. In certain embodiments, the MDM2 inhibitor as a single-agent maintenance therapy is administered for a cycle of about one week, about two weeks, about three weeks, about four weeks, about five weeks, about six weeks, about eight weeks, or about ten weeks, with a rest period of about 1 day to about four weeks. In certain embodiments, the MDM2 inhibitor as a single-agent maintenance therapy is administered for a cycle of three weeks, four weeks, five weeks, or six weeks with a rest period of 1, 3, 5, 7, 9, 12, or 14. In certain embodiments, the rest period is 7 days. In certain embodiments, the rest period is 14 days. In certain embodiments, the rest period is a period that is sufficient for bone marrow recovery. The frequency, number, and length of dosing cycles can be increased or decreased.

In certain embodiments, the MDM2 inhibitor as a single-agent maintenance therapy is administered for two weeks in a 21-day cycle with a 7-day rest period. In certain embodiments, the MDM2 inhibitor as a single-agent maintenance therapy is administered for two weeks in a 21-day cycle with a 7-day rest period, wherein the MDM2 inhibitor is administered every other day. In certain embodiments, the MDM2 inhibitor as a single-agent maintenance therapy is administered for two weeks in a 21-day cycle with a 7-day rest period, wherein the MDM2 inhibitor is administered on Days 1, 3, 5, 7, 9, 11, and 13.

In certain embodiments, the MDM2 inhibitor as a single-agent maintenance therapy is administered for three weeks in a 28-day cycle with a 7-day rest period. In certain embodiments, the MDM2 inhibitor as a single-agent maintenance therapy is administered for three weeks in a 28-day cycle with a 7-day rest period, wherein the MDM2 inhibitor is administered every other day and the platinum compound is administered once. In certain embodiments, the MDM2 inhibitor as a single-agent maintenance therapy is administered for three weeks in a 28-day cycle with a 7-day rest period, wherein the MDM2 inhibitor is administered on Days 1, 3, 5, 7, 9, 11, 13, 15, 17, 19, and 21.

In certain embodiments, the MDM2 inhibitor as a single-agent maintenance therapy is administered in an amount ranging from about 0.1 mg/kg every other day to about 10 mg/kg per day, from about 0.2 mg/kg every other day to about 5 mg/kg per day, or from about 0.5 mg/kg every other day to about 5 mg/kg per day. In one embodiment, the MDM2 inhibitor as a single-agent maintenance therapy is administered in an amount ranging from about 0.1 mg/kg every other day to about 10 mg/kg per day. In another embodiment, the MDM2 inhibitor as a single-agent maintenance therapy is administered in an amount ranging from about 0.2 mg/kg every other day to about 5 mg/kg per day. In yet another embodiment, the MDM2 inhibitor as a single-agent maintenance therapy is administered in an amount ranging from about 0.5 mg/kg every other day to about 5 mg/kg per day.

In certain embodiments, the MDM2 inhibitor as a single-agent maintenance therapy is administered in an amount ranging from about 0.1 to about 10 mg/kg per day, from about 0.2 to about 5 mg/kg per day, or from about 0.5 to about 5 mg/kg per day. In one embodiment, the MDM2 inhibitor as a single-agent maintenance therapy is administered in an amount ranging from about 0.1 to about 10 mg/kg per day. In another embodiment, the MDM2 inhibitor as a single-agent maintenance therapy is administered in an amount ranging from about 0.2 to about 5 mg/kg per day. In yet another embodiment, the MDM2 inhibitor as a single-agent maintenance therapy is administered in an amount ranging from about 0.5 to about 5 mg/kg per day. In still another embodiment, the MDM2 inhibitor as a single-agent maintenance therapy is administered in an amount ranging from about 0.5, about 0.6, about 0.7, about 0.8, about 0.9, about 1, about 1.2, about 1.3, about 1.4, about 1.5, about 1.6, about 1.7, about 1.8, about 1.9, about 2, about 2.1, about 2.2, about 2.3, about 2.4, or about 2.5 mg/kg per day.

In certain embodiments, the MDM2 inhibitor as a single-agent maintenance therapy is administered in an amount ranging from about 0.1 to about 10 mg/kg every other day, from about 0.2 to about 5 mg/kg every other day, or from about 0.5 to about 5 mg/kg every other day. In one embodiment, the MDM2 inhibitor as a single-agent maintenance therapy is administered in an amount ranging from about 0.1 to about 10 mg/kg every other day. In another embodiment, the MDM2 inhibitor as a single-agent maintenance therapy is administered in an amount ranging from about 0.2 to about 5 mg/kg every other day. In yet another embodiment, the MDM2 inhibitor as a single-agent maintenance therapy is administered in an amount ranging from about 0.5 to about 5 mg/kg every other day. In still another embodiment, the MDM2 inhibitor as a single-agent maintenance therapy is administered in an amount ranging from about 0.5, about 0.6, about 0.7, about 0.8, about 0.9, about 1, about 1.2, about 1.3, about 1.4, about 1.5, about 1.6, about 1.7, about 1.8, about 1.9, about 2, about 2.1, about 2.2, about 2.3, about 2.4, or about 2.5 mg/kg every other day.

In certain embodiments, the MDM2 inhibitor as a single-agent maintenance therapy is administered in an amount ranging from about 1 mg every other day to about 1,000 mg per day, from about 2 mg every other day to about 500 mg per day, from about 5 mg every other day to about 250 mg per day, or from about 10 mg every other day to about 200 mg per day. In one embodiment, the MDM2 inhibitor as a single-agent maintenance therapy is administered in an amount ranging from about 1 mg every other day to about 1,000 mg per day. In another embodiment, the MDM2 inhibitor as a single-agent maintenance therapy is administered in an amount ranging from about 2 mg every other day to about 500 mg per day. In yet another embodiment, the MDM2 inhibitor as a single-agent maintenance therapy is administered in an amount ranging from about 5 mg every other day to about 250 mg per day. In yet another embodiment the MDM2 inhibitor as a single-agent maintenance therapy is administered in an amount ranging from about 10 mg every other day to about 200 mg per day.

In certain embodiments, the MDM2 inhibitor as a single-agent maintenance therapy is administered in an amount ranging from about 1 to about 1,000 mg per day, from about 2 to about 500 mg per day, from about 5 to about 250 mg per day, or from about 10 to about 200 mg per day. In one embodiment, the MDM2 inhibitor as a single-agent maintenance therapy is administered in an amount ranging from about 1 to about 1,000 mg per day. In another embodiment, the MDM2 inhibitor as a single-agent maintenance therapy is administered in an amount ranging from about 2 to about 500 mg per day. In yet another embodiment, the MDM2 inhibitor as a single-agent maintenance therapy is administered in an amount ranging from about 5 to about 250 mg per day. In yet another embodiment, the MDM2 inhibitor as a single-agent maintenance therapy is administered in an amount ranging from about 10 to about 200 mg per day. In still another embodiment, the MDM2 inhibitor as a single-agent maintenance therapy is administered in an amount ranging from about 10, about 20, about 50, about 60, about 70, about 80, about 90, about 100, about 110, about 120, about 130, about 140, about 150, about 160, about 170, about 180, about 190, or 200 mg per day.

In certain embodiments, the MDM2 inhibitor as a single-agent maintenance therapy is administered in an amount ranging from about 1 to about 1,000 mg every other day, from about 2 to about 500 mg every other day, from about 5 to about 250 mg every other day, or from about 10 to about 200 mg every other day. In one embodiment, the MDM2 inhibitor as a single-agent maintenance therapy is administered in an amount ranging from about 1 to about 1,000 mg every other day. In another embodiment, the MDM2 inhibitor as a single-agent maintenance therapy is administered in an amount ranging from about 2 to about 500 mg every other day. In yet another embodiment, the MDM2 inhibitor as a single-agent maintenance therapy is administered in an amount ranging from about 5 to about 250 mg every other day. In yet another embodiment, the MDM2 inhibitor as a single-agent maintenance therapy is administered in an amount ranging from about 10 to about 200 mg every other day. In still another embodiment, the MDM2 inhibitor as a single-agent maintenance therapy is administered in an amount ranging from about 10, about 20, about 50, about 60, about 70, about 80, about 90, about 100, about 110, about 120, about 130, about 140, about 150, about 160, about 170, about 180, about 190, or 200 mg every other day.

In certain embodiments, the subject is treated with an MDM2 inhibitor as a single-agent maintenance therapy from about 1 to about 50, from about 2 to about 20, from about 2 to 10, or from about 4 to about 8. In certain embodiments, the subject is treated with an MDM2 inhibitor as a single-agent maintenance therapy from about 1 to about 50 cycles. In certain embodiments, the subject is treated with an MDM2 inhibitor as a single-agent maintenance therapy from about 2 to about 20 cycles. In certain embodiments, the subject is treated with an MDM2 inhibitor as a single-agent maintenance therapy from about 2 to 10 cycles. In certain embodiments, the subject is treated with an MDM2 inhibitor as a single-agent maintenance therapy from about 4 to about 8 cycles.

In one embodiment, provided herein is a method of inhibiting the growth of a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound.

In another embodiment, provided herein is a method of modulating the activity of MDM2 in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound.

In yet another embodiment, provided herein is a method of modulating an MDM2/p53 interaction in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound. In one embodiment, the cell has a functional p53. In another embodiment, the cell has a wild-type p53.

In still another embodiment, provided herein is a method of inducing apoptosis in a cell, comprising contacting the cell with (i) an effective amount of an MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; and (ii) an effective amount of a platinum compound.

In one embodiment, the cell is a cancerous cell. In another embodiment, the cell is a cell of solid cancer. In yet another embodiment, the cell is a salivary gland cancer cell. In yet another embodiment, the cell is a cell of stage I, stage II, stage III, or stage IV salivary gland cancer. In still another embodiment, the cell is a cell of stage VIA, stage VIB, or stage VIC salivary gland cancer.

In one embodiment, the cell is a cell of acinic cell carcinoma, adenoid cystic carcinoma, adenocarcinoma NOS, mucoepidermoid carcinoma, or polymorphous adenocarcinoma. In another embodiment, the cell is a cell of adenosquamous carcinoma, basal cell adenocarcinoma, carcinoma ex pleomorphic adenoma, carcinosarcoma, clear cell carcinoma, cystadenocarcinoma, epithelial-myoepithelial carcinoma, lymphoepithelial carcinoma, myoepithelial carcinoma, oncocytic carcinoma, poorly differentiated carcinoma, salivary duct carcinoma, sebaceous adenocarcinoma, secretory carcinoma, or squamous cell carcinoma. In yet another embodiment, the cell is a cell of mucoepidermoid carcinoma, adenoid cystic carcinoma, acinic cell carcinoma, carcinoma ex pleomorphic adenoma, squamous cell carcinoma, or adenocarcinoma. In still another embodiment, the cell is a cell of mucoepidermoid carcinoma, acinic cell carcinoma, polymorphous adenocarcinoma, or epithelial-myoepithelial carcinoma.

In certain embodiments, the cell is a cell of metastatic cancer. In certain embodiments, the cell is a cell of drug-resistant cancer. In certain embodiments, the cell is a cell of multidrug-resistant cancer. In certain embodiments, the cell is a cell of cancer resistant to carboplatin, cisplatin, cyclophosphamide, docetaxel, doxorubicin, 5-fluorouracil, methotrexate, paclitaxel, or vinorelbine.

In one embodiment, the cell has a non-pathogenic p53. In another embodiment, the cell has a functional p53. In yet another embodiment, the cell has a wild-type p53. In yet another embodiment, the cell does not have a pathogenic p53. In still another embodiment, the cell does not have a non-functional p53.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); mmol (millimoles); h (hour or hours); and min (minutes).

Example 1

Multicenter Phase I/II Trial of an MDM2 Inhibitor With or Without Platinum Chemotherapy in p53 Wild-Type Salivary Gland Carcinoma A phase I/II trial is conducted to evaluate the efficacy of compound A8 (i.e., 4-((3'R,4'S,5'R)-6"-chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]-octane-1-carboxylic acid) in the presence or absence of carboplatin in treating a p53 wild-type malignant salivary gland.

This is an open label multi-institution phase I/II study with an initial randomized phase (Part 1), followed by a planned single-arm phase (Part 2). The study enrolls approximately 62 subjects. In the initial randomized phase (Part 1), subjects are randomized to one of two arms: 14 subjects assigned to Arm A (treatment with compound A8 alone) and 28 subjects assigned to Arm B (treatment with compound A8 and carboplatin). Subjects in Arm A each receive a starting dose (150 mg) of compound A8 orally within one hour after food on Days 1, 3, 5, 7, 9, 11, and 13 in a 21-day cycle. Subjects in Arm B each receive a starting dose (150 mg) of compound A8 orally within one hour after food on Days 1, 3, 5, 7, 9, 11, and 13 and a starting dose of carboplatin intravenously at AUC 4.5 on Day 1 in a 21-day cycle. Doses for subsequent subjects in both arms are determined by the TITE-CRM (time-to-event continual reassessment method) algorithm at 50 mg, 100 mg, or 150 mg.

Based on the outcomes of the two arms in Part 1, a single arm is selected for further study in Part 2. Response rate (defined as CR or PR after two treatment cycles) is the foremost consideration in deciding on the most promising arm for Part 2; in addition, a comprehensive evaluation of available data including toxicity and PK data are also considered. After an arm has been chosen to advance, additional 20 subjects are accrued in Part 2.

The arm with subjects with an ongoing response to treatment (i.e., stable disease, partial response, or complete response) after 6 cycles is selected for further study in Part 2. The subjects in the selected arm are treated orally with compound A8 (150 mg) as single-agent maintenance therapy on Days 1, 3, 5, 7, 9, 11, and 13 in a 21-day cycle.

Subjects are monitored closely for toxicity and undergo imaging to evaluate efficacy once every 3 cycles.

Eligible subjects for the study are the ones between 18 years or older with a histologically documented malignant salivary gland cancer with or without a metastasis, not amenable to curative treatment; or documentation of patient refusal of curative treatment. Additional inclusion criteria for the eligible subjects include (i) no evidence of a p53 mutation in previous mutational testing; (ii) ECOG performance status of no greater than 1; (iii) presence of measurable disease by CT scan per RECIST v1.1 with greater than 20% increase in tumor burden in the preceding 12 months; (iv) life expectancy of no less than 12 weeks; and (v) adequate organ and marrow function obtained ≤2 weeks prior to enrollment. Furthermore, the eligible subjects have adequate bone marrow, hepatic, renal, and cardiac function (including WBC ~3×10$^9$ cells/mL, ANC ~1.5×10$^9$ cell/mL, platelets ~100,000 cells/mm$^3$, hemoglobin ~9.0 g/dL, concentrations of total serum bilirubin within 1.5× upper limit of normal (ULN) unless the subject has documented Gilberts syndrome, AST, ALT within 2,5× institutional upper limits of normal unless there are liver metastases in which case AST and ALT within 5.0×ULN, serum creatinine clearance ~30 mL/min, PT/INR<1.5× ULN or PTT (aPTT) <1.5×LIN (unless abnormalities are unrelated to coagulopathy or bleeding disorder).

The study excludes those who have received (i) a prior treatment with MDM2 inhibitors; (ii) any systemic anti-cancer therapy (including chemotherapy and/or hormone therapy) for salivary gland cancer within 4 weeks of the start of the study; or (iii) a live vaccine or an antiretroviral drug within 4 weeks of the start of the study; or (iv) who have a progressive disease with platinum-based chemotherapy within the last 6 months. The study also excludes those who have received (i) within 7 days of the start of the study, a CYP3A4 inhibitor, including, but not limited to, clarithromycin, itraconazole, ketoconazole, grapefruit juice, indinavir, nelfinavir, ritonavir, nefazodone, saquinavir, and telithromycin; or a P-gp inhibitor, including, but not limited to, amiodarone, carvedilol, profafenone, quinidine, verapamil, ranolazine, and ritonarvir; or (ii) a CYP3A4 inducer, including, but not limited to, rifampin, carbamazepine, enzalutamide, mitotane, phenytoin, and St. John's wort within 25 days of the start of the study.

Subjects in each arm are monitored using the time-to-event continual reassessment method (TITE-CRM). Dose-limiting toxicity (DLT) is determined via CTCAE version 5.0 based on the rate of drug-related grade 3-5 adverse events experienced within the first 6 weeks (2 cycles) of the study. Maximally tolerated dose (MTD) is also determined based on DLTs observed during the first 6 weeks (2 cycles) of the study. Overall response rate is determined via RECIST v1.1 for treatment up to 12 months as the proportion of the eligible subjects achieving either complete response (CR) or partial response (PR).

Adverse effects associated with the treatment are documented. Progress free survival (PFS), duration of response (DoR), overall survival (OS), and disease control rate (DCR) in subjects with p53 wild type malignant salivary gland cancers are determined in the study. Overall response rate (ORR) is determined by tumor histology (ACC vs. non-ACC)

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating, or alleviating one or more symptoms of a disorder, disease, or condition mediated by an MDM2 or an MDM2/p53 interaction in a subject, comprising administering to the subject a therapeutically effective amount of an MDM2 inhibitor and a therapeutically effective amount of a platinum compound; wherein the MDM2 inhibitor is a compound of Formula (I):

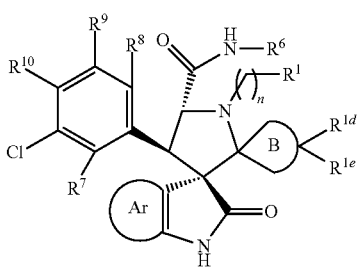
(I)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

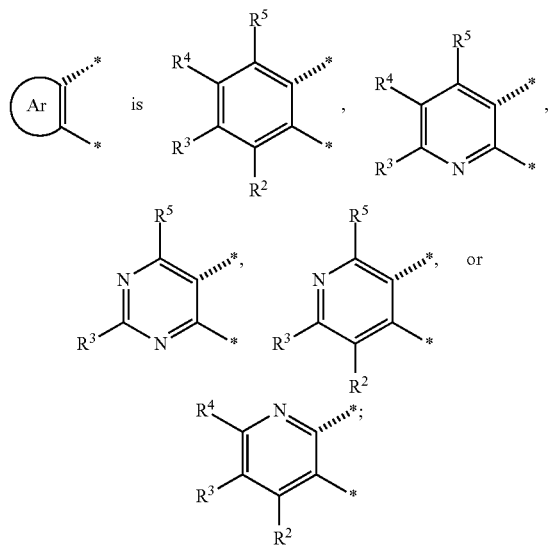

ring B is $C_{3-10}$ cycloalkyl or heterocyclyl;
$R^1$ is hydrogen, $C_{1-6}$ alkyl, $C_{3-10}$ cycloalkyl, heterocyclyl, $-NR^{1b}R^{1c}$, or $-OR^{1a}$;
n is an integer of 0, 1, or 2;
$R^2$, $R^3$, $R^4$, $R^5$, $R^7$, $R^8$, $R^9$, and $R^{10}$ are each independently hydrogen, fluoro, chloro, methyl, or trifluoromethyl;
$R^6$ is

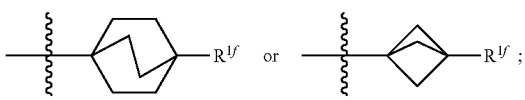

wherein each $R^{1f}$ is independently $-C(=O)OR^{1a}$, $-C(=O)NR^{1b}R^{1c}$, $-C(=O)NHSO_2CH_3$;
$R^{1d}$ and $R^{1c}$ are each independently hydrogen, halo, $C_{1-6}$ alkyl, or $-OR^{1a}$; or $R^{1d}$ and $R^{1e}$ together with the carbon to which they are attached form $C_{3-10}$ cycloalkyl or heterocyclyl; and
each $R^{1a}$, $R^{1b}$, and $R^{1c}$ is independently hydrogen or $C_{1-6}$ alkyl;
wherein each alkyl, cycloalkyl, and heterocyclyl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents $Q^a$; and (c) $-C(O)R^a$, $-C(O)OR^a$, $-C(O)NR^bR^c$, $-C(O)SR^a$, $-C(NR^a)NR^bR^c$, $-C(S)R^a$, $-C(S)OR^a$, $-C(S)NR^bR^c$, $-OR^a$, $-OC(O)R^a$, $-OC(O)OR^a$, $-OC(O)NR^bR^c$, $-OC(O)SR^a$, $-OC(=NR^a)NR^bR^c$, $-OC(S)R^a$, $-OC(S)OR^a$, $-OC(S)NR^bR^c$, $-OS(O)R^a$, $-OS(O)_2R^a$, $-OS(O)NR^bR^c$, $-OS(O)_2NR^bR^c$, $-NR^bR^c$, $-NR^aC(O)R^d$, $-NR^aC(O)OR^d$, $-NR^aC(O)NR^bR^c$, $-NR^aC(O)SR^d$, $-NR^aC(=NR^d)NR^bR^c$, $-NR^aC(S)R^d$, $-NR^aC(S)OR^d$, $-NR^aC(S)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl, optionally substituted with one or more substituents $Q^a$;
wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(O)SR^e$, $-C(NR^e)NR^fR^g$, $-C(S)R^e$, $-C(S)OR^e$, $-C(S)NR^fR^g$, $-OR^e$, $-OC(O)R^e$, $-OC(O)OR^e$, $-OC(O)NR^fR^g$, $-OC(O)SR^e$, $-OC(=NR^e)NR^fR^g$, $-OC(S)R^e$, $-OC(S)OR^e$, $-OC(S)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(O)SR^f$, $-NR^eC(=NR^h)NR^fR^g$, $-NR^eC(S)R^h$, $-NR^eC(S)OR^f$, $-NR^eC(S)NR^fR^g$, $-NR^eS(O)R^h$, $-NR^e S(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

2. The method of claim 1, wherein the disorder, disease, or condition is cancer.

3. The method of claim 2, wherein the cancer is solid cancer.

4. The method of claim 3, wherein the cancer is salivary gland cancer.

5. The method of claim 4, wherein the salivary gland cancer is mucoepidermoid carcinoma, adenoid cystic carcinoma, acinic cell carcinoma, carcinoma ex pleomorphic adenoma, squamous cell carcinoma, or adenocarcinoma.

6. The method of claim 2, wherein the cancer has a functional p53 or a wild-type p53; or wherein the cancer is metastatic, refractory, relapsed, or drug-resistant.

7. The method of claim 1, wherein the MDM2 inhibitor is:
3-((3'R,4'S,5'R)-6"-chloro-4'-(3-chloro-2-fluorophenyl)-2"-oxodispiro-[cyclohexane-1,2'-pyrrolidine-3',3"-indoline]-5'-carboxamido)bicyclo[1.1.1]pentane-1-carboxylic acid A1;
4-((3'R,4'S,5'R)-6"-chloro-4'-(3-chloro-2-fluorophenyl)-2"-oxodispiro-[cyclohexane-1,2'-pyrrolidine-3',3"-indoline]-5'-carboxamido)bicyclo[2.2.2]octane-1-carboxylic acid A2;

4-((3'R,4'S,5'R)-6"-chloro-4'-(3-chloro-2-fluorophenyl)-4,4-difluoro-2"-oxodispiro-[cyclo-hexane-1,2'-pyrrolidine-3',3"-indoline]-5'-carboxamido)bicycle-[2.2.2]octane-1-carboxylic acid A3;

(3'R,4'S,5'R)-6"-chloro-4'-(3-chloro-2-fluorophenyl)-N-(4-((methylsulfonyl)-carbamoyl)-bicyclo[2.2.2]octan-1-yl)-2"-oxodispiro[cyclohexane-1,2'-pyrrolidine-3',3"-indoline]-5'-carboxamide A4;

4-((1r,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A5;

4-((1s,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A6;

(3'R,4'S,5'R)—N-(4-carbamoylbicyclo[2.2.2]octan-1-yl)-6"-chloro-4'-(3-chloro-2-fluorophenyl)-1'-methyl-2"-oxodispiro[cyclohexane-1,2'-pyrrolidine-3',3"-indoline]-5'-carboxamide A7;

4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8;

4-((3'R,4'S,5'R)-6"-chloro-4'-(3-chloro-2-fluorophenyl)-1'-methyl-2"-oxodispiro-[cyclohexane-1,2'-pyrrolidine-3',3"-indoline]-5'-carboxamido)-bicyclo[2.2.2]octane-1-carboxylic acid A9;

4-((3'R,4'S,5'R)-6"-chloro-4'-(3-chloro-2-fluorophenyl)-3,3-dimethyl-2"-oxodispiro[cyclobutane-1,2'-pyrrolidine-3',3"-indoline]-5'-carboxamido)bicyclo[2.2.2]octane-1-carboxylic acid A10;

4-((3'R,4'S,5'R)-6"-chloro-4'-(3-chloro-2-fluorophenyl)-1',3,3-trimethyl-2"-oxodispiro[cyclobutane-1,2'-pyrrolidine-3',3"-indoline]-5'-carboxamido)bicyclo[2.2.2]octane-1-carboxylic acid A11;

4-((3'R,4'S,5'R)-6"-chloro-4'-(3-chloro-2-fluorophenyl)-2"-oxo-1",2"-dihydrodispiro[cyclohexane-1,2'-pyrrolidine-3',3"-pyrrolo[3,2-c]pyridine]-5'-carboxamido)bicyclo[2.2.2]octane-1-carboxylic acid A12;

4-((3'R,4'S,5'R)-6"-chloro-4'-(3-chloro-2-fluorophenyl)-1'-methyl-2"-oxo-1",2"-dihydrodispiro[cyclohexane-1,2'-pyrrolidine-3',3"-pyrrolo[3,2-c]pyridine]-5'-carboxamido)bicyclo[2.2.2]octane-1-carboxylic acid A13;

4-((3'R,4'S,5'R)-6"-chloro-4'-(3-chloro-2-fluorophenyl)-3,3-dimethyl-2"-oxo-1",2"-dihydrodispiro[cyclobutane-1,2'-pyrrolidine-3',3"-pyrrolo[3,2-c]pyridine]-5'-carboxamido)bicyclo[2.2.2]octane-1-carboxylic acid A14; or 4-((3'R,4'S,5'R)-6"-chloro-4'-(3-chloro-2-fluorophenyl)-1',3,3-trimethyl-2"-oxo-1",2"-dihydrodispiro[cyclobutane-1,2'-pyrrolidine-3',3"-pyrrolo[3,2-c]pyridine]-5'-carboxamido)bicyclo[2.2.2]octane-1-carboxylic acid A15;

or a tautomer, a mixture of two or more tautomers, or an isotopic variant thereof; or a pharmaceutically acceptable salt, solvate, or hydrate thereof.

8. The method of claim 1, wherein the MDM2 inhibitor is 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8 of the formula:

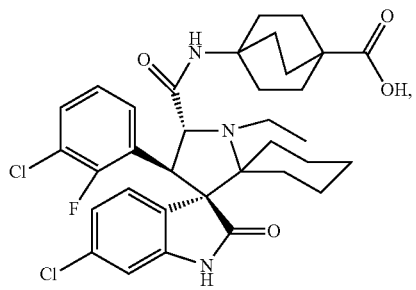 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a tautomer, a mixture of two or more tautomers, or an isotopic variant thereof; or a pharmaceutically acceptable salt, solvate, or hydrate thereof.

9. The method of claim 1, wherein the MDM2 inhibitor is provided as a pharmaceutical composition, which comprises the MDM2 inhibitor and a pharmaceutically acceptable excipient;

wherein the MDM2 inhibitor is formulated as a single oral dosage form;

wherein the MDM2 inhibitor is formulated as a tablet or capsule;

wherein the MDM2 inhibitor is administered orally;

wherein the therapeutically effective amount of the MDM2 inhibitor is ranging from about 0.1 mg/kg every other day to about 10 mg/kg per day; or wherein the therapeutically effective amount of the MDM2 inhibitor is ranging from about 1 mg every other day to about 1,000 mg per day.

10. The method of claim 1, wherein the platinum is an antineoplastic compound.

11. The method of claim 1, wherein the platinum compound is carboplatin, cisplatin, ethacraplatin, heptaplatin, iproplatin, lobaplatin, mitaplatin, nedaplatin, ormaplatin, oxaliplatin, phenanthriplatin, picoplatin, pyriplatin, satrplatin, or triplatin tetranitrate.

12. The method of claim 1, wherein the platinum compound is administered parenterally or intravenously;

wherein the platinum compound is administered in an amount resulting in an area under a curve (AUC) ranging from about 1 to about 10 mg/mL/min; or wherein the therapeutically effect amount of the platinum compound is ranging from about 1 mg/m$^2$ every four weeks to 1,000 mg/m$^2$ every week.

13. The method of claim 1, wherein the MDM2 inhibitor is administered in a 21-day cycle;

wherein the MDM2 inhibitor is administered every other day;

wherein the MDM2 inhibitor is administered on Days 1, 3, 5, 7, 9, 11, and 13 in a 21-day cycle;

wherein the platinum compound is administered in a 21-day cycle;

wherein the platinum compound is administered once in a 21-day cycle; or wherein the platinum compound is administered on Day 1 in a 21-day cycle.

14. The method of claim 1, wherein the method comprises administering to the subject in a 21-day cycle: (i) 4-((3'R, 4'S,5'R)-6"-chloro-4'-(3-chloro-2-fluorophenyl)-1'-ethyl-2"- oxodispiro-[cyclohexane-1,2'-pyrrolidine-3',3"-indoline]-5'-carboxamido)bicyclo[2.2.2]-octane-1-carboxylic acid A8 of the formula:

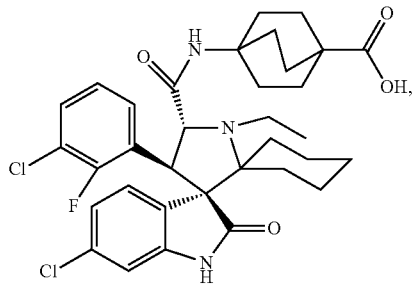 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

and (ii) carboplatin; wherein compound A8 is administered every other day for two weeks and carboplatin is administered once.

15. The method of claim 14, wherein compound A8 is administered on Days 1, 3, 5, 7, 9, 11, and 13; and carboplatin is administered on Day 1.

16. The method of claim 14, wherein compound A8 is administered in an amount ranging from about 20 to about 500 mg every other day for two weeks.

17. The method of claim 14, wherein compound A8 is administered in an amount of about 50, about 100, about 150, or about 200 mg every other day for two weeks.

18. The method of claim 14, wherein carboplatin is administered in an amount resulting in an AUC ranging from about 4 to about 6 mg/mL/min.

19. The method of claim 14, wherein carboplatin is administered in an amount resulting in an AUC of about 4, about 4.5, about 5, about 5.5, or about 6 mg/mL/min.

20. The method of claim 1, wherein the subject is a human.

* * * * *

UNITED STATES PATENT AND TRADEMARK OFFICE
CERTIFICATE OF CORRECTION

PATENT NO. : 11,850,239 B2
APPLICATION NO. : 17/127131
DATED : December 26, 2023
INVENTOR(S) : Yifan Zhai and Dajun Yang It is certified that error appears in the above-identified patent and that said Letters Patent is hereby corrected as shown below:

In the Specification

In Column 55, Line 58 (part of Claim 1), replace "$R^{1c}$" with "$R^{1e}$".

Signed and Sealed this
Twenty-seventh Day of February, 2024

Katherine Kelly Vidal
*Director of the United States Patent and Trademark Office*